US010584156B2

(12) United States Patent
Weiss

(10) Patent No.: US 10,584,156 B2
(45) Date of Patent: Mar. 10, 2020

(54) INSULIN ANALOGUES WITH A GLUCOSE-REGULATED CONFORMATIONAL SWITCH

(71) Applicant: CASE WESTERN RESERVE UNIVERSITY, Cleveland, OH (US)

(72) Inventor: Michael Weiss, Moreland Hills, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/558,030

(22) PCT Filed: Mar. 14, 2016

(86) PCT No.: PCT/US2016/022390

§ 371 (c)(1),
(2) Date: Sep. 13, 2017

(87) PCT Pub. No.: WO2016/149222

PCT Pub. Date: Sep. 22, 2016

(65) Prior Publication Data

US 2018/0057559 A1 Mar. 1, 2018

Related U.S. Application Data

(60) Provisional application No. 62/133,251, filed on Mar. 13, 2015, provisional application No. 62/132,704, filed on Mar. 13, 2015.

(51) Int. Cl.
*A61K 38/00* (2006.01)
*C07K 14/62* (2006.01)

(52) U.S. Cl.
CPC ............ *C07K 14/62* (2013.01); *C07K 14/622* (2013.01); *A61K 38/00* (2013.01)

(58) Field of Classification Search
None
See application file for complete search history.

(56) References Cited

U.S. PATENT DOCUMENTS 8,569,231 B2 * 10/2013 Zion ...................... A61K 38/28
514/5.9

FOREIGN PATENT DOCUMENTS

| | | |
|---|---|---|
| WO | 2001/092334 | 12/2001 |
| WO | 2003/048195 | 6/2003 |
| WO | 2010/107520 | 9/2010 |
| WO | 2014/015078 | 1/2014 |
| WO | 2014/093696 | 5/2014 |
| WO | 2014/093696 | 6/2014 |

OTHER PUBLICATIONS

Hoeg-Jensen, Thomas et al., "Insulins with built-in glucose sensors for glucose responsive insulin release," Journal of Peptide Science, Nov. 1, 2004, vol. 11, pp. 339-346.

Hoeg-Jensen, Thomas et al., "Reversible Insulin Self-Assembly under Carbohydrate Control," Journal of American Chemical Society, Nov. 17, 2005, vol. 127, pp. 6158-6159.

Webber, Matthew J. et al., "Engineering Synthetically Modified Insulin for Glucose-Responsive Diabetes Therapy," Expert Rev Endocrinol Metab, Author Manuscript, Aug. 25, 2016.

* cited by examiner

*Primary Examiner* — Jeanette M Lieb

(74) *Attorney, Agent, or Firm* — Hahn Loeser & Parks, LLP; John J. Cunniff

(57) ABSTRACT

A two-chain insulin analogue contains an A chain modified by (i) a monomeric glucose-binding element at or near its N terminus and (ii) a B chain modified by at or near its C terminus by an element that reversibly binds to the monomeric glucose-binding element such that this linkage is displaceable by glucose. The monomeric glucose-binding element may be phenylboronic acid derivative (optionally halogenated). The B chain may be modified by a diol-containing element derived from a monosaccharide, disaccharide or oligosaccharide, a non-saccharide diol-containing moiety or a α-hydroxycarboxylate-containing moiety. The analogue can be manufactured by trypsin-mediated semi-synthesis. Formulations can be at strengths U-10 to U-1000 in soluble solutions at pH 7.0-8.0 with or without zinc ions at a molar ratio of 0.0-3.0 ions per insulin analogue monomer. A patient with diabetes mellitus may be treated with subcutaneous, intraperitoneal, or oral administration of a physiologically effective amount of the insulin analogue.

20 Claims, 8 Drawing Sheets

Specification includes a Sequence Listing.

PROINSULIN

MODEL

SEQUENCE LISTING

```
<160> NUMBER OF SEQ ID NOS: 53

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85


<210> SEQ ID NO 2
<211> LENGTH: 21
```

<212> TYPE: PRT
<213> ORGANISM: Homo sapiens

<400> SEQUENCE: 2

Gly Ile Val Glu Gln Cys Cys Thr Ser Ile Cys Ser Leu Tyr Gln Leu
1 5 10 15

Glu Asn Tyr Cys Asn
20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1 5 10 15

Leu Val Cys Gly Glu Arg Gly Phe Phe Tyr Thr Pro Lys Thr
20 25 30

<210> SEQ ID NO 4
<211> LENGTH: 30
<212> TYPE: PRT
<213> ORGANISM: Homo sapiens

<400> SEQUENCE: 4

Phe Val Glu Gln His Leu Cys Gly Ser His Leu Val Glu Ala Leu Tyr
1 5 10 15

Leu Val Cys Gly Glu Arg Gly Phe Phe Tyr Thr Lys Pro Thr
20 25 30

<210> SEQ ID NO 5
<211> LENGTH: 32
<212> TYPE: PRT
<213> ORGANISM: Homo sapiens

<400> SEQUENCE: 5

Phe Val Glu Gln His Leu Cys Gly Ser His Leu Val Glu Ala Leu Tyr
1 5 10 15

Leu Val Cys Gly Glu Arg Gly Phe Phe Tyr Thr Lys Pro Thr Glu Glu
20 25 30

<210> SEQ ID NO 6
<211> LENGTH: 30
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa is an amino acid
<220> FEATURE:
<221> NAME/KEY: MISC_FEATURE
<222> LOCATION: (29)..(29)
<223> OTHER INFORMATION: Xaa is Ornithine

<400> SEQUENCE: 6

Phe Val Glu Gln His Leu Cys Gly Ser Xaa Leu Val Glu Ala Leu Tyr
1 5 10 15

Leu Val Cys Gly Glu Arg Gly Phe Phe Tyr Thr Pro Xaa Thr
20 25 30

<210> SEQ ID NO 7
<211> LENGTH: 32
<212> TYPE: PRT

-continued

```
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic
      acid moiety or halogenic derivative of a phenylboronic acid moiety
      connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta fluoro Phe, 2
      chloro Phe, 2 bromo Phe, 4 chloro Phe, 2 methyl Phe, or
      Cyclohexanylalanine
<220> FEATURE:
<221> NAME/KEY: MISC_FEATURE
<222> LOCATION: (27)..(27)
<223> OTHER INFORMATION: Xaa is Thr or Ser linked to one or more
      saccharide subunits selected from alpha-D mannopyranoside, alpha-D
      glucopyranoside, N acetyl b D galactopyranoside
<220> FEATURE:
<221> NAME/KEY: MISC_FEATURE
<222> LOCATION: (29)..(29)
<223> OTHER INFORMATION: Xaa is Lysine, Ornithine, Arginine, di amino
      butyric acid, di amino propionic acid, Norleucine, aminobutyric
      acid, aminopropionic acid, Alanine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 7

Xaa Val Glu Gln His Leu Cys Gly Ser His Leu Val Glu Ala Leu Tyr
1               5                   10                  15

Leu Val Cys Gly Glu Arg Gly Xaa Phe Tyr Xaa Pro Xaa Thr Xaa Xaa
            20                  25                  30


<210> SEQ ID NO 8
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic
      acid moiety or halogenic derivative of a phenylboronic acid moiety
      connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta fluoro Phe, 2
      chloro Phe, 2 bromo Phe, 4 chloro Phe, 2 methyl Phe, or
      Cyclohexanylalanine
<220> FEATURE:
<221> NAME/KEY: MISC_FEATURE
<222> LOCATION: (27)..(27)
<223> OTHER INFORMATION: Xaa is Thr or Ser linked to one or more
      saccharide subunits selected from alpha-D mannopyranoside, alpha-D
      glucopyranoside, N acetyl b D galactopyranoside
<220> FEATURE:
<221> NAME/KEY: MISC_FEATURE
<222> LOCATION: (28)..(28)
<223> OTHER INFORMATION: Xaa is Lysine, Arginine, Ornithine, di
      aminobutyric acid, di aminopropionic acid, Alanine, Aspartic Acid,
      or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 8

Xaa Val Glu Gln His Leu Cys Gly Ser His Leu Val Glu Ala Leu Tyr
```

-continued

```
1               5                   10                  15

Leu Val Cys Gly Glu Arg Gly Xaa Phe Tyr Xaa Xaa Pro Thr Xaa Xaa
            20                  25                  30


<210> SEQ ID NO 9
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic
      acid moiety or halogenic derivative of a phenylboronic acid moiety
      connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta fluoro Phe, 2
      chloro Phe, 2 bromo Phe, 4 chloro Phe, 2 methyl Phe, or
      Cyclohexanylalanine
<220> FEATURE:
<221> NAME/KEY: MISC_FEATURE
<222> LOCATION: (27)..(27)
<223> OTHER INFORMATION: Xaa is Asn or Gln linked to one or more
      saccharide subunits selected from alpha-D mannopyranoside, alpha-D
      glucopyranoside, N acetyl b D galactopyranoside
<220> FEATURE:
<221> NAME/KEY: MISC_FEATURE
<222> LOCATION: (29)..(29)
<223> OTHER INFORMATION: Xaa is Lysine, Ornithine, Arginine, di amino
      butyric acid, di amino propionic acid, Norleucine, aminobutyric
      acid, aminopropionic acid, Alanine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 9

Xaa Val Glu Gln His Leu Cys Gly Ser His Leu Val Glu Ala Leu Tyr
1               5                   10                  15

Leu Val Cys Gly Glu Arg Gly Xaa Phe Tyr Xaa Pro Xaa Thr Xaa Xaa
            20                  25                  30


<210> SEQ ID NO 10
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic
      acid moiety or halogenic derivative of a phenylboronic acid moiety
      connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta fluoro Phe, 2
      chloro Phe, 2 bromo Phe, 4 chloro Phe, 2 methyl Phe, or
      Cyclohexanylalanine
<220> FEATURE:
<221> NAME/KEY: MISC_FEATURE
<222> LOCATION: (27)..(27)
<223> OTHER INFORMATION: Xaa is Asn or Gln linked to one or more
      saccharide subunits selected from alpha-D mannopyranoside, alpha-D
      glucopyranoside, N acetyl b D galactopyranoside
<220> FEATURE:
<221> NAME/KEY: MISC_FEATURE
<222> LOCATION: (28)..(28)
<223> OTHER INFORMATION: Xaa is Lysine, Arginine, Ornithine, di
      aminobutyric acid, di aminopropionic acid, Alanine, Aspartic Acid,
      or Glutamic Acid
<220> FEATURE:
```

```
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 10

Xaa Val Glu Gln His Leu Cys Gly Ser His Leu Val Glu Ala Leu Tyr
1               5                   10                  15

Leu Val Cys Gly Glu Arg Gly Xaa Phe Tyr Xaa Xaa Pro Thr Xaa Xaa
            20                  25                  30


<210> SEQ ID NO 11
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (27)..(27)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent
<220> FEATURE:
<221> NAME/KEY: MISC_FEATURE
<222> LOCATION: (29)..(29)
<223> OTHER INFORMATION: Xaa is an Arginine, Alanine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 11

Xaa Val Glu Gln His Leu Cys Gly Ser His Leu Val Glu Ala Leu Tyr
1               5                   10                  15

Leu Val Cys Gly Glu Arg Gly Xaa Phe Tyr Xaa Pro Xaa Thr Xaa Xaa
            20                  25                  30


<210> SEQ ID NO 12
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (27)..(27)
```

-continued

<223> OTHER INFORMATION: Xaa is a derivative of the D or L stereoisomer of Lysine, Ornithine, di-aminobutyric acid or di-aminopropionic acid whose side chain amino group is linked to a diol-containing reagent
<220> FEATURE:
<221> NAME/KEY: MISC_FEATURE
<222> LOCATION: (28)..(28)
<223> OTHER INFORMATION: Xaa is Arginine, Alanine, Aspartic Acid, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 12

Xaa Val Glu Gln His Leu Cys Gly Ser His Leu Val Glu Ala Leu Tyr
1 5 10 15

Leu Val Cys Gly Glu Arg Gly Xaa Phe Tyr Xaa Xaa Pro Thr Xaa Xaa
20 25 30

<210> SEQ ID NO 13
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (27)..(27)
<223> OTHER INFORMATION: Xaa is a derivative of the D or L stereoisomer of Cysteine or Homocysteine whose side-chain sulfur atom is linked to a diol-containing reagent
<220> FEATURE:
<221> NAME/KEY: MISC_FEATURE
<222> LOCATION: (29)..(29)
<223> OTHER INFORMATION: Xaa is an Arginine, di-amino-butyric acid, di-amino-propionic acid, Norleucine, aminobutyric acid, aminopropionic acid, Alanine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 13

Xaa Val Glu Gln His Leu Cys Gly Ser His Leu Val Glu Ala Leu Tyr
1 5 10 15

Leu Val Cys Gly Glu Arg Gly Xaa Phe Tyr Xaa Pro Xaa Thr Xaa Xaa
20 25 30

<210> SEQ ID NO 14
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (27)..(27)
<223> OTHER INFORMATION: Xaa is a derivative of the D or L stereoisomer of Cysteine or Homocysteine whose side-chain sulfur atom is linked to a diol-containing reagent
<220> FEATURE:
<221> NAME/KEY: MISC_FEATURE
<222> LOCATION: (28)..(28)
<223> OTHER INFORMATION: Xaa is Arginine, Ornithine, di-aminobutyric acid, di-aminopropionic acid, Alanine, Aspartic Acid, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 14

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Xaa Xaa Pro Thr Xaa Xaa
            20                  25                  30
```

<210> SEQ ID NO 15
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine, di-amino-butyric acid, di-amino-propionic acid, Norleucine, aminobutyric acid, aminopropionic acid, Alanine, or Glutamic Acid
<220> FEATURE:
<221> NAME/KEY: MISC_FEATURE
<222> LOCATION: (30)..(30)
<223> OTHER INFORMATION: Xaa is Thr or Ser linked to one or more saccharide subunits selected from alpha-D-mannopyranoside, alpha-D-glucopyranoside, N-acetyl-b-D-galactopyranoside
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 15

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Xaa Xaa Xaa
            20                  25                  30
```

```
<210> SEQ ID NO 16
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Lysine, Arginine, Ornithine,
      di-aminobutyric acid, di-aminopropionic acid, Alanine, Aspartic
      Acid, or Glutamic Acid
<220> FEATURE:
<221> NAME/KEY: MISC_FEATURE
<222> LOCATION: (30)..(30)
<223> OTHER INFORMATION: Xaa is Thr or Ser linked to one or more
      saccharide subunits selected from alpha-D-mannopyranoside,
      alpha-D-glucopyranoside, N-acetyl-b-D-galactopyranoside
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 16

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Xaa Xaa Xaa
            20                  25                  30


<210> SEQ ID NO 17
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine,
      di-amino-butyric acid, di-amino-propionic acid, Norleucine,
      aminobutyric acid, aminopropionic acid, Alanine, or Glutamic Acid
<220> FEATURE:
<221> NAME/KEY: MISC_FEATURE
<222> LOCATION: (30)..(30)
<223> OTHER INFORMATION: Xaa is Asn or Gln linked to one or more
      saccharide subunits selected from alpha-D-mannopyranoside,
      alpha-D-glucopyranoside, N-acetyl-b-D-galactopyranoside
<220> FEATURE:
<221> NAME/KEY: MISC_FEATURE
<222> LOCATION: (31)..(32)
```

<223> OTHER INFORMATION: Xaa Xaa is 0-2 amino acids selected from Glu, Gln, Gly, Ala, or Ser and if present, at least one amino acid is Glutamic Acid

<400> SEQUENCE: 17

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Xaa Xaa Xaa
            20                  25                  30
```

<210> SEQ ID NO 18
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Lysine, Arginine, Ornithine, di-aminobutyric acid, di-aminopropionic acid, Alanine, Aspartic Acid, or Glutamic Acid
<220> FEATURE:
<221> NAME/KEY: MISC_FEATURE
<222> LOCATION: (30)..(30)
<223> OTHER INFORMATION: Xaa is Asn or Gln linked to one or more saccharide subunits selected from alpha-D-mannopyranoside, alpha-D-glucopyranoside, N-acetyl-b-D-galactopyranoside
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 18

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Xaa Xaa Xaa
            20                  25                  30
```

<210> SEQ ID NO 19
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (29)..(29)
<223> OTHER INFORMATION: Xaa is Alanine, Arginine, Aspartic Acid or Glutamic Acid
<220> FEATURE:
<221> NAME/KEY: MISC_FEATURE
<222> LOCATION: (30)..(30)
<223> OTHER INFORMATION: Xaa is a derivative of the D or L stereoisomer of Lysine, Ornithine, di-aminobutyric acid or di-aminopropionic acid whose side chain amino group is linked to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 19

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Xaa Xaa Xaa
            20                  25                  30
```

<210> SEQ ID NO 20
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Alanine, Arginine, Aspartic Acid, or Glutamic Acid
<220> FEATURE:
<221> NAME/KEY: MISC_FEATURE
<222> LOCATION: (30)..(30)
<223> OTHER INFORMATION: Xaa is a derivative of the D or L stereoisomer of Lysine, Ornithine, di-aminobutyric acid or di-aminopropionic acid whose side chain amino group is linked to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 20

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Xaa Xaa Xaa
            20                  25                  30
```

<210> SEQ ID NO 21
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional

```
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (29)..(29)
<223> OTHER INFORMATION: Xaa is Alanine, Arginine, Aspartic Acid or
      Glutamic Acid
<220> FEATURE:
<221> NAME/KEY: MISC_FEATURE
<222> LOCATION: (30)..(30)
<223> OTHER INFORMATION: Xaa is a derivative of the D or L stereoisomer
      of Cysteine or Homocysteine whose side-chain sulfur atom is linked
      to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 21

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Xaa Xaa Xaa
            20                  25                  30


<210> SEQ ID NO 22
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Alanine, Arginine, Aspartic Acid, or
      Glutamic Acid
<220> FEATURE:
<221> NAME/KEY: MISC_FEATURE
<222> LOCATION: (30)..(30)
<223> OTHER INFORMATION: Xaa is a derivative of the D or L stereoisomer
      of Cysteine or Homocysteine whose side-chain sulfur atom is linked
      to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 22

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Xaa Xaa Xaa
            20                  25                  30


<210> SEQ ID NO 23
```

```
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine,
      di-amino-butyric acid, di-amino-propionic acid, Norleucine,
      aminobutyric acid, aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Thr or Ser linked to one or more
      saccharide subunits selected from alpha-D-mannopyranoside,
      alpha-D-glucopyranoside, N-acetyl-Beta-D-galactopyranoside
<220> FEATURE:
<221> NAME/KEY: MISC_FEATURE
<222> LOCATION: (32)..(32)
<223> OTHER INFORMATION: Xaa is Glu, Gln, Gly, Ala, or Ser

<400> SEQUENCE: 23

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30


<210> SEQ ID NO 24
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Lysine, Arginine, Ornithine,
      di-aminobutyric acid, di-aminopropionic acid, Alanine, Aspartic
      Acid, or Glutamic Acid
<220> FEATURE:
<221> NAME/KEY: MISC_FEATURE
<222> LOCATION: (31)..(31)
<223> OTHER INFORMATION: Xaa is Asn or Gln linked to one or more
      saccharide subunits selected from alpha-D-mannopyranoside,
      alpha-D-glucopyranoside, N-acetyl- Beta-D-galactopyranoside
<220> FEATURE:
<221> NAME/KEY: MISC_FEATURE
<222> LOCATION: (32)..(32)
<223> OTHER INFORMATION: Xaa is Glu, Gln, Gly, Ala, or Ser

<400> SEQUENCE: 24

Xaa Val Glu Gln His Leu Cys Gly Ser His Leu Val Glu Ala Leu Tyr
```

-continued

```
1               5                   10                  15

Leu Val Cys Gly Glu Arg Gly Xaa Phe Tyr Thr Xaa Pro Thr Xaa Xaa
            20                  25                  30


<210> SEQ ID NO 25
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine,
      di-amino-butyric acid, di-amino-propionic acid, Norleucine,
      aminobutyric acid, aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Asn or Gln linked to one or more
      saccharide subunits selected from alpha-D-mannopyranoside,
      alpha-D-glucopyranoside, N-acetyl- Beta-D-galactopyranoside
<220> FEATURE:
<221> NAME/KEY: MISC_FEATURE
<222> LOCATION: (32)..(32)
<223> OTHER INFORMATION: Xaa is Glu, Gln, Gly, Ala, or Ser

<400> SEQUENCE: 25

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30


<210> SEQ ID NO 26
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Lysine, Ornithine, Arginine,
      di-aminobutyric acid, di-amino-propionic acid, Norleucine,
      aminobutyric acid, aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Asn or Gln linked to one or more
      saccharide subunits selected from alpha-D-mannopyranoside,
      alpha-D-glucopyranoside, N-acetyl- Beta-D-galactopyranoside
<220> FEATURE:
```

<221> NAME/KEY: MISC_FEATURE
<222> LOCATION: (32)..(32)
<223> OTHER INFORMATION: Xaa is Glu, Gln, Gly, Ala, or Ser

<400> SEQUENCE: 26

Xaa Val Glu Gln His Leu Cys Gly Ser His Leu Val Glu Ala Leu Tyr
1 5 10 15

Leu Val Cys Gly Glu Arg Gly Xaa Phe Tyr Thr Xaa Pro Thr Xaa Xaa
20 25 30

<210> SEQ ID NO 27
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine, di-amino-butyric acid, di-amino-propionic acid, Norleucine, aminobutyric acid, aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid or Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer of Lysine, Ornithine, di-aminobutyric acid or di-aminopropionic acid whose side chain amino group is linked to a diol-containing reagent or is Glu, Gln, Gly, Ala, or Ser

<400> SEQUENCE: 27

Xaa Val Glu Gln His Leu Cys Gly Ser His Leu Val Glu Ala Leu Tyr
1 5 10 15

Leu Val Cys Gly Glu Arg Gly Xaa Phe Tyr Thr Pro Xaa Thr Xaa Xaa
20 25 30

<210> SEQ ID NO 28
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Alanine, Arginine, Aspartic Acid, or

```
      Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid or
      Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent or Glu, Gln, Gly, Ala, or Ser

<400> SEQUENCE: 28

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Thr Xaa Xaa
            20                  25                  30


<210> SEQ ID NO 29
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (29)..(29)
<223> OTHER INFORMATION: Xaa is Arginine, Norleucine, aminobutyric acid,
      aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid or
      Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent

<400> SEQUENCE: 29

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30


<210> SEQ ID NO 30
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
```

<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Alanine, Arginine, Aspartic Acid, or Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid or Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer of Lysine, Ornithine, di-aminobutyric acid or di-aminopropionic acid whose side chain amino group is linked to a diol-containing reagent

<400> SEQUENCE: 30

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Thr Xaa Xaa
            20                  25                  30
```

<210> SEQ ID NO 31
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (29)..(29)
<223> OTHER INFORMATION: Xaa is Lysine, Ornithine, Arginine, di-amino-butyric acid, di-amino-propionic acid, Norleucine, aminobutyric acid, aminopropionic acid, Alanine, or Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid or Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer of Cysteine or Homocysteine whose side-chain sulfur atom is linked to a diol-containing reagent

<400> SEQUENCE: 31

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30
```

<210> SEQ ID NO 32
<211> LENGTH: 32
<212> TYPE: PRT

<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Alanine, Arginine, Aspartic Acid, or Glutamic Acid
<220> FEATURE:
<221> NAME/KEY: MISC_FEATURE
<222> LOCATION: (31)..(31)
<223> OTHER INFORMATION: Xaa is Alanine, Arginine, Aspartic Acid, or Glutamic Acid
<220> FEATURE:
<221> NAME/KEY: MISC_FEATURE
<222> LOCATION: (32)..(32)
<223> OTHER INFORMATION: Xaa is a derivative of the D or L stereoisomer of Cysteine or Homocysteine whose side-chain sulfur atom is linked to a diol-containing reagent

<400> SEQUENCE: 32

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Pro Thr Xaa Xaa
            20                  25                  30
```

<210> SEQ ID NO 33
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Proline, Alanine, Arginine, Aspartic Acid, or Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer of Lysine, Ornithine, di-aminobutyric acid or di-aminopropionic acid whose side chain amino group is linked to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu, Gln, Gly, Ala, or Ser and if present, at least one amino acid is Glutamic Acid

<400> SEQUENCE: 33

```
Xaa Val Glu Gln His Leu Cys Gly Ser His Leu Val Glu Ala Leu Tyr
```

-continued

```
1               5                   10                  15

Leu Val Cys Gly Glu Arg Gly Xaa Phe Tyr Thr Xaa Xaa Thr Xaa Xaa
            20                  25                  30


<210> SEQ ID NO 34
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Proline, Alanine, Arginine, Aspartic
      Acid, or Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent

<400> SEQUENCE: 34

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa
            20                  25


<210> SEQ ID NO 35
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Proline, Lysine, Ornithine, Arginine,
      di-amino-butyric acid, di-amino-propionic acid, Norleucine,
      aminobutyric acid, aminopropionic acid, Alanine, Aspartic Acid or
      Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer
      of Cysteine or Homocysteine whose side-chain sulfur atom is linked
      to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu,
```

Gln, Gly, Ala, or Ser and if present, at least one amino acid is Glutamic Acid

<400> SEQUENCE: 35

Xaa Val Glu Gln His Leu Cys Gly Ser His Leu Val Glu Ala Leu Tyr
1 5 10 15

Leu Val Cys Gly Glu Arg Gly Xaa Phe Tyr Thr Xaa Xaa Thr Xaa Xaa
20 25 30

<210> SEQ ID NO 36
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is Proline, Lysine, Ornithine, Arginine, di-amino-butyric acid, di-amino-propionic acid, Norleucine, aminobutyric acid, aminopropionic acid, Alanine, Aspartic Acid or Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer of Cysteine or Homocysteine whose side-chain sulfur atom is linked to a diol-containing reagent

<400> SEQUENCE: 36

Xaa Val Glu Gln His Leu Cys Gly Ser His Leu Val Glu Ala Leu Tyr
1 5 10 15

Leu Val Cys Gly Glu Arg Gly Xaa Phe Tyr Thr Xaa Xaa
20 25

<210> SEQ ID NO 37
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a phenylboronic-acid moiety or halogenic derivative of a phenylboronic-acid moiety connected by peptide linkage or optional acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe, 2-chloro-Phe, 2-bromo-Phe, 4-chloro-Phe, 2-methyl-Phe, or Cyclohexanylalanine
<220> FEATURE:
<221> NAME/KEY: MISC_FEATURE
<222> LOCATION: (28)..(28)
<223> OTHER INFORMATION: Xaa is a derivative of the D or L stereoisomer of Cysteine or Homocysteine whose side-chain sulfur atom is linked to a diol-containing reagent
<220> FEATURE:
<221> NAME/KEY: MISC_FEATURE
<222> LOCATION: (29)..(29)
<223> OTHER INFORMATION: Xaa is Lysine, Proline, Arginine, Alanine,

```
      Arginine, Aspartic Acid, Glutamic Acid, Norleucine, aminobutyric
      acid, aminopropionic acid, Ornithine, di-aminobutyric acid, or
      di-aminopropionic acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 37

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 38
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: MISC_FEATURE
<222> LOCATION: (28)..(28)
<223> OTHER INFORMATION: Xaa is a derivative of the D or L stereoisomer
      of Cysteine or Homocysteine whose side-chain sulfur atom is linked
      to a diol-containing reagent
<220> FEATURE:
<221> NAME/KEY: MISC_FEATURE
<222> LOCATION: (29)..(29)
<223> OTHER INFORMATION: Xaa is Lysine, Proline, Arginine, Alanine,
      Arginine, Aspartic Acid, Glutamic Acid, Norleucine, aminobutyric
      acid, aminopropionic acid, Ornithine, di-aminobutyric acid, or
      di-aminopropionic acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 38

Xaa Phe Val Glu Gln His Leu Cys Gly Ser His Leu Val Glu Ala Leu
1               5                   10                  15

Tyr Leu Val Cys Gly Glu Arg Gly Xaa Phe Tyr Thr Xaa Xaa
            20                  25                  30


<210> SEQ ID NO 39
<211> LENGTH: 28
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
```

```
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is a derivative of the D or L stereoisomer
      of Cysteine or Homocysteine whose side-chain sulfur atom is linked
      to a diol-containing reagent

<400> SEQUENCE: 39

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa
            20                  25


<210> SEQ ID NO 40
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 40

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 41
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
```

```
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent
<220> FEATURE:
<221> NAME/KEY: MISC_FEATURE
<222> LOCATION: (29)..(29)
<223> OTHER INFORMATION: Xaa is Lysine, Proline, Arginine, Alanine,
      Arginine, Aspartic Acid, Glutamic Acid, Norleucine, aminobutyric
      acid, aminopropionic acid, Ornithine, di-aminobutyric acid, or
      di-aminopropionic acid

<400> SEQUENCE: 41

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa
            20                  25


<210> SEQ ID NO 42
<211> LENGTH: 28
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent

<400> SEQUENCE: 42

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa
            20                  25


<210> SEQ ID NO 43
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
```

```
<221> NAME/KEY: MISC_FEATURE
<222> LOCATION: (28)..(28)
<223> OTHER INFORMATION: Xaa is Proline, Alanine, Arginine, Aspartic
      Acid, or Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 43

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 44
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Proline, Alanine, Arginine, Aspartic
      Acid, or Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer
      of Lysine, Ornithine, di-aminobutyric acid or di-aminopropionic
      acid whose side chain amino group is linked to a diol-containing
      reagent

<400> SEQUENCE: 44

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa
            20                  25


<210> SEQ ID NO 45
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
```

```
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Lysine, Ornithine, Arginine,
      di-amino-butyric acid, di-amino-propionic acid, Norleucine,
      aminobutyric acid, aminopropionic acid, Alanine, Aspartic Acid or
      Glutamic Acid
<220> FEATURE:
<221> NAME/KEY: MISC_FEATURE
<222> LOCATION: (29)..(29)
<223> OTHER INFORMATION: Xaa is a derivative of the D or L stereoisomer
      of Cysteine or Homocysteine whose side-chain sulfur atom is linked
      to a diol-containing reagent
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 45

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 46
<211> LENGTH: 29
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Lysine, Ornithine, Arginine,
      di-amino-butyric acid, di-amino-propionic acid, Norleucine,
      aminobutyric acid, aminopropionic acid, Alanine, Aspartic Acid or
      Glutamic Acid
<220> FEATURE:
<221> NAME/KEY: MISC_FEATURE
<222> LOCATION: (29)..(29)
<223> OTHER INFORMATION: Xaa isa derivative of the D or L stereoisomer
      of Cysteine or Homocysteine whose side-chain sulfur atom is linked
      to a diol-containing reagent

<400> SEQUENCE: 46

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa
            20                  25


<210> SEQ ID NO 47
<211> LENGTH: 32
<212> TYPE: PRT
<213> ORGANISM: Homo sapiens
<220> FEATURE:
<221> NAME/KEY: MISC_FEATURE
```

```
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Thr or Ser linked to one or more
      saccharide subunits selected from alpha-D-mannopyranoside,
      alpha-D-glucopyranoside, N-acetyl-b-D-galactopyranoside
<220> FEATURE:
<221> NAME/KEY: MISC_FEATURE
<222> LOCATION: (29)..(29)
<223> OTHER INFORMATION: Xaa is Arginine, Ornithine, di-aminobutyric
      acid, di-aminopropionic acid, Proline, Alanine, Aspartic Acid,
      Glutamine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 47

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 48
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Asn or Gln linked to one or more
      saccharide subunits selected from alpha-D-mannopyranoside,
      alpha-D-glucopyranoside, N-acetyl-b-D-galactopyranoside
<220> FEATURE:
<221> NAME/KEY: MISC_FEATURE
<222> LOCATION: (29)..(29)
<223> OTHER INFORMATION: Xaa is Arginine, Ornithine, di-aminobutyric
      acid, di-aminopropionic acid, Proline, Alanine, Aspartic Acid,
      Glutamine, or Glutamic Acid
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 48

Xaa Val Glu Gln His Leu Cys Gly Ser His Leu Val Glu Ala Leu Tyr
1               5                   10                  15
```

-continued

```
Leu Val Cys Gly Glu Arg Gly Xaa Phe Tyr Thr Xaa Xaa Thr Xaa Xaa
            20                  25                  30


<210> SEQ ID NO 49
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Arginine, Ornithine, di-aminobutyric
      acid, di-aminopropionic acid, Proline, Alanine, Aspartic Acid,
      Glutamine, or Glutamic Acid
<220> FEATURE:
<221> NAME/KEY: MISC_FEATURE
<222> LOCATION: (29)..(29)
<223> OTHER INFORMATION: Xaa is Thr or Ser linked to one or more
      saccharide subunits selected from alpha-D-mannopyranoside,
      alpha-D-glucopyranoside, N-acetyl-b-D-galactopyranoside
<220> FEATURE:
<221> NAME/KEY: MISC_FEATURE
<222> LOCATION: (31)..(32)
<223> OTHER INFORMATION: Xaa Xaa is 0-2 amino acids selected from Glu,
      Gln, Gly, Ala, or Ser and if present, at least one amino acid is
      Glutamic Acid

<400> SEQUENCE: 49

Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30


<210> SEQ ID NO 50
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Phe or Phe modified with a
      phenylboronic-acid moiety or halogenic derivative of a
      phenylboronic-acid moiety connected by peptide linkage or optional
      acyl linker
<220> FEATURE:
<221> NAME/KEY: MISC_FEATURE
<222> LOCATION: (24)..(24)
<223> OTHER INFORMATION: Xaa is Phenylalanine, penta-fluoro-Phe,
      2-chloro-Phe, 2-bromo-Phe, 4-chloro-Phe, 2-methyl-Phe, or
      Cyclohexanylalanine
<220> FEATURE:
<221> NAME/KEY: MISC_FEATURE
<222> LOCATION: (28)..(28)
<223> OTHER INFORMATION: Xaa is Arginine, Ornithine, di-aminobutyric
      acid, di-aminopropionic acid, Proline, Alanine, Aspartic Acid,
      Glutamine, or Glutamic Acid
<220> FEATURE:
<221> NAME/KEY: MISC_FEATURE
<222> LOCATION: (29)..(29)
<223> OTHER INFORMATION: Xaa is Asn or Gln linked to one or more
      saccharide subunits selected from alpha-D-mannopyranoside,
      alpha-D-glucopyranoside, N-acetyl-b-D-galactopyranoside
```

<220> FEATURE:
<221> NAME/KEY: MISC_FEATURE
<222> LOCATION: (31)..(32)
<223> OTHER INFORMATION: Xaa Xaa is 0-2 amino acids selected from Glu,
Gln, Gly, Ala, or Ser and if present, at least one amino acid is
Glutamic Acid

<400> SEQUENCE: 50

```
Xaa Val Glu Gln His Leu Cys Gly Ser His Leu Val Glu Ala Leu Tyr
1               5                   10                  15

Leu Val Cys Gly Glu Arg Gly Xaa Phe Tyr Thr Xaa Xaa Thr Xaa Xaa
            20                  25                  30
```

<210> SEQ ID NO 51
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is Gly or Gly modified with a
phenylboronic-acid moiety or halogenic derivative of a
phenylboronic-acid moiety connected by peptide linkage or optional
acyl linker to the a-amino group of Gly
<220> FEATURE:
<221> NAME/KEY: MISC_FEATURE
<222> LOCATION: (8)..(8)
<223> OTHER INFORMATION: Xaa is Threonine, Alanine, Histidine,
Glutamine, Arginine, or Glutamic Acid
<220> FEATURE:
<221> NAME/KEY: MISC_FEATURE
<222> LOCATION: (13)..(13)
<223> OTHER INFORMATION: Xaa is Leu or Trp
<220> FEATURE:
<221> NAME/KEY: MISC_FEATURE
<222> LOCATION: (14)..(14)
<223> OTHER INFORMATION: Xaa is Tyrosine, Alanine or Glutamic Acid
<220> FEATURE:
<221> NAME/KEY: MISC_FEATURE
<222> LOCATION: (17)..(17)
<223> OTHER INFORMATION: Xaa is Glutamic Acid, Glutamine or Arginine
<220> FEATURE:
<221> NAME/KEY: MISC_FEATURE
<222> LOCATION: (21)..(21)
<223> OTHER INFORMATION: Xaa is Asparagine, Aspartic Acid, Alanine or
Glycine

<400> SEQUENCE: 51

```
Xaa Ile Val Glu Gln Cys Cys Xaa Ser Ile Cys Ser Xaa Xaa Gln Leu
1               5                   10                  15

Xaa Asn Tyr Cys Xaa
            20
```

<210> SEQ ID NO 52
<211> LENGTH: 21
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is a phenylboronic-acid moiety or halogenic
derivative of a phenylboronic-acid moiety connected by to the
side-chain amino group of Lysine, Ornithine, di-aminobutyric acid
or di-aminopropionic acid
<220> FEATURE:
<221> NAME/KEY: MISC_FEATURE
<222> LOCATION: (8)..(8)
<223> OTHER INFORMATION: Xaa is Threonine, Alanine, Histidine,
Glutamine, Arginine, or Glutamic Acid
<220> FEATURE:
<221> NAME/KEY: MISC_FEATURE
<222> LOCATION: (13)..(13)
<223> OTHER INFORMATION: Xaa is Leu or Trp
<220> FEATURE:
<221> NAME/KEY: MISC_FEATURE
<222> LOCATION: (14)..(14)
<223> OTHER INFORMATION: Xaa is Tyrosine, Alanine or Glutamic Acid
<220> FEATURE:
<221> NAME/KEY: MISC_FEATURE
<222> LOCATION: (17)..(17)
<223> OTHER INFORMATION: Xaa is Glutamic Acid, Glutamine or Arginine
<220> FEATURE:
<221> NAME/KEY: MISC_FEATURE
<222> LOCATION: (21)..(21)
<223> OTHER INFORMATION: Xaa is Asparagine, Aspartic Acid, Alanine or Glycine

<400> SEQUENCE: 52

```
Gly Ile Val Xaa Gln Cys Cys Xaa Ser Ile Cys Ser Xaa Xaa Gln Leu
1               5                   10                  15

Xaa Asn Tyr Cys Xaa
            20
```

<210> SEQ ID NO 53
<211> LENGTH: 21
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is a basic residue selected from the group consisting of D- or L-Lys, D- or L-Orn, D- or L-di-aminopropionic acid derivatized by a phenylboronic acid moiety optionally including a halogenic modification and optionally attached via an acyl linker
<220> FEATURE:
<221> NAME/KEY: MISC_FEATURE
<222> LOCATION: (8)..(8)
<223> OTHER INFORMATION: Xaa is Threonine, Alanine, Histidine, Glutamine, Arginine, or Glutamic Acid
<220> FEATURE:
<221> NAME/KEY: MISC_FEATURE
<222> LOCATION: (13)..(13)
<223> OTHER INFORMATION: Xaa is Leu or Trp
<220> FEATURE:
<221> NAME/KEY: MISC_FEATURE
<222> LOCATION: (14)..(14)
<223> OTHER INFORMATION: Xaa is Tyrosine, Alanine or Glutamic Acid
<220> FEATURE:
<221> NAME/KEY: MISC_FEATURE
<222> LOCATION: (17)..(17)
<223> OTHER INFORMATION: Xaa is Glutamic Acid, Glutamine or Arginine
<220> FEATURE:
<221> NAME/KEY: MISC_FEATURE
<222> LOCATION: (21)..(21)
<223> OTHER INFORMATION: Xaa is Asparagine, Aspartic Acid, Alanine or Glycine

<400> SEQUENCE: 53

```
Xaa Ile Val Glu Gln Cys Cys Xaa Ser Ile Cys Ser Xaa Xaa Gln Leu
1               5                   10                  15

Xaa Asn Tyr Cys Xaa
            20
```

INSULIN ANALOGUES WITH A GLUCOSE-REGULATED CONFORMATIONAL SWITCH

STATEMENT REGARDING FEDERALLY SPONSORED RESEARCH OR DEVELOPMENT

This invention was made with government support under cooperative agreements awarded by the National Institutes of Health under grant number DK040949. The U.S. government has certain rights to the invention.

BACKGROUND OF THE INVENTION

This invention relates to polypeptide hormone analogues that contain a glucose-conformational switch and so exhibit glucose-responsive rates of hormone disassembly or glucose-responsive binding to cognate cellular receptors. Application to insulin is described in relation to the treatment of patients and non-human mammals with Type 1 or Type 2 diabetes mellitus by subcutaneous, intraperitoneal or intravenous injection. The insulin analogues of the present invention may also exhibit other enhanced pharmaceutical properties, such as increased thermodynamic stability, augmented resistance to thermal fibrillation above room temperature, decreased mitogenicity, and/or altered pharmacokinetic and pharmacodynamic properties. More particularly, this invention relates to insulin analogues that confer either rapid action (relative to wild-type insulin in its regular soluble formulation), intermediate action (comparable to NPH insulin formulations known in the art) or protracted action (comparable to basal insulins known in the art as exemplified by insulin detemir and insulin glargine) such that the affinity of the said analogues for the insulin receptor is higher when dissolved in a solution containing glucose at a concentration above the physiological range (>140 mg/dl; hyperglycemia) than when dissolved in a solution containing glucose at a concentration below the physiological range (<80 mg/dl; hypoglycemia).

The engineering of non-standard proteins, including therapeutic agents and vaccines, may have broad medical and societal benefits. Naturally occurring proteins as encoded in the genomes of human beings, other mammals, vertebrate organisms, invertebrate organisms, or eukaryotic cells in general—may have evolved to function optimally within a cellular context but may be suboptimal for therapeutic applications. Analogues of such proteins may exhibit improved biophysical, biochemical, or biological properties. A benefit of protein analogues would be to achieve enhanced activity (such as metabolic regulation of metabolism leading to reduction in blood-glucose concentration under conditions of hyperglycemia) with decreased unfavorable effects (such as induction of hypoglycemia or its exacerbation). An example of a therapeutic protein is provided by insulin. Wild-type human insulin and insulin molecules encoded in the genomes of other mammals bind to insulin receptors is multiple organs and diverse types of cells, irrespective of the receptor isoform generated by alternative modes of RNA splicing or by alternative patterns of post-translational glycosylation. An example of a medical benefit would be the non-standard design of a soluble insulin analogue whose intrinsic affinity for insulin receptors on the surface of target cells, and hence whose biological potency, would depend on the concentration of glucose in the blood stream.

The insulin molecule contains two chains, an A chain, containing 21 residues, and a B chain containing 30 residues. The mature hormone is derived from a longer single-chain precursor, designated proinsulin, as outlined in FIG. 1. Specific residues in the insulin molecule are indicated by the amino-acid type (typically in standard three-letter code; e.g., Lys and Ala indicate Lysine and Alanine) and in superscript the chain (A or B) and position in that chain. For example, Alanine at position 14 of the B chain of human insulin is indicated by $Ala^{B14}$; and likewise Lysine at position B28 of insulin lispro (the active component of Humalog®; Eli Lilly and Co.) is indicated by $Lys^{B28}$. Although the hormone is stored in the pancreatic β-cell as a $Zn^{2+}$-stabilized hexamer, it functions as a $Zn^{2+}$-free monomer in the bloodstream. Administration of insulin has long been established as a treatment for diabetes mellitus. A major goal of conventional insulin replacement therapy in patients with diabetes mellitus is tight control of the blood glucose concentration to prevent its excursion above or below the normal range characteristic of healthy human subjects. Excursions above the normal range are associated with increased long-term risk of microvascular disease, including retinapathy, blindness, and renal failure. Hypoglycemia in patients with diabetes mellitus is a frequent complication of insulin replacement therapy and when severe can lead to significant morbidity (including altered mental status, loss of consciousness, seizures, and death). Indeed, fear of such complications poses a major barrier to efforts by patients (and physicians) to obtain rigorous control of blood glucose concentrations (i.e., excusions within or just above the normal range), and in patients with long-established Type 2 diabetes mellitus such efforts ("tight control") may lead to increased mortally. In addition to the above consequences of severe hypoglycemia (designated neuroglycopenic effects), mild hypoglycemia may activate counter-regulatory mechanisms, including over-activation of the sympathetic nervous system leading to turn to anxiety and tremulousness (symptoms designated adrenergic). Patients with diabetes mellitus may not exhibit such warning signs, however, a condition known as hypoglycemic unawareness. The absence of symptoms of mild hypoglycemia increases the risk of major hypoglycemia and its associated morbidity and mortality. Multiple and recurrent episodes of hypoglycemia are also associated with chronic cognitive decline, a proposed mechanism underlying the increased prevalence of dementia in patients with long-standing diabetes mellitus. There is therefore an urgent need for new diabetes treatment technologies that would reduce the risk of hypoglycemia while preventing upward excursions in blood-glucose concentration above the normal range.

Diverse technologies have been developed in an effort to mitigate the threat of hypoglycemia in patients treated with insulin. Foundational to all such efforts is education of the patient (and also members of his or her family) regarding the symptoms of hypoglycemia and following the recognition of such symptoms, the urgency of the need to ingest a food or liquid rich in glucose, sucrose, or other rapidly digested form of carbohydrate; an example is provided by orange juice supplemented with sucrose (cain sugar). This baseline approach has been extended by the development of specific diabetes-oriented products, such as squeezable tubes containing an emulsion containing glucose in a form that can be rapidly absorbed through the mucous membranes of the mouth, throat, stomach, and small intestine. Preparations of the counter-regulatory hormone glucagon, provided as a powder, have likewise been developed in a form amenable to rapid dissolution and subcutaneous injection as an emergency treatment of severe hypoglycemia. Insulin pumps have been linked to a continuous glucose monitor such that subcutaneous injection of insulin is halted and an alarm is sounded when hypoglycemic readings of the interstitial glucose concentration are encountered. Such a device-based approach has led to the experimental testing of closed-loop systems in which the pump and monitor are combined with a computer-based algorithm as an "artificial pancreas."

For more than three decades, there has been interest in the development of glucose-responsive materials for co-administration with an insulin analogue or modified insulin molecule such that the rate of release of the hormone from the subcutaneous depot depends on the interstitial glucose concentration. Such systems in general contain a glucose-responsive polymer, gel or other encapsulation material; and may also require a derivative of insulin containing a modification that enables binding of the hormone to the above material. An increase in the ambient concentration of glucose in the interstitial fluid at the site of subcutaneous injection may displace the bound insulin or insulin derivative either by competitive displacement of the hormone or by physical-chemical changes in the properties of the polymer, gel or other encapsulation material. The goal of such systems is to provide an intrinsic autoregulation feature to the encapsulated or gel-coated subcutaneous depot such that the risk of hypoglycemia is mitigated through delayed release of insulin when the ambient concentration of glucose is within or below the normal range. To date, no such glucose-responsive systems are in clinical use.

A recent technology exploits the structure of a modified insulin molecule, optionally in conjunction with a carrier molecule such that the complex between the modified insulin molecule and the carrier is soluble and may enter into the bloodstream. This concept differs from glucose-responsive depots in which the polymer, gel or other encapsulation material remains in the subcutaneous depot as the free hormone enters into the bloodstream. An embodiment of this approach is known in the art wherein the A chain is modified at or near its N-terminus (utilizing the α-amino group of residue A1 or via the ε-amino group of a Lysine substituted at positions A2, A3, A4 or A5) to contain an "affinity ligand" (defined as a saccharide moiety), the B chain is modified at its or near N-terminus (utilizing the α-amino group of residue B1 or via the ε-amino group of a Lysine substituted at positions B2, B3, B4 or B5) to contain a "monovalent glucose-binding agent." In this description the large size of the exemplified or envisaged glucose-binding agents (monomeric lectin domains, DNA aptamers, or peptide aptomers) restricted their placement to the N-terminal segment of the B chain as defined above. In the absence of exogenous glucose or other exogenous saccharide, intramolecular interactions between the A1-linked affinity ligand and B1-linked glucose-binding agent was envisaged to "close" the structure of the hormone and thereby impair its activity. Only modest glucose-responsive properties of this class of molecular designs were reported (Zion et al., 2012).

The suboptimal properties of insulin analogs modified at or near residue A1 by an affinity ligand and simultaneously modified at or near residue B1 by a large glucose-binding agent (i.e., of size similar or greater than that of an insulin A or B chain), are likely to be intrinsic to this class of molecular designs. Indeed, the rationale for such designs relied on the low activity of insulin analogs containing short chemical cross-links between the α-amino groups of residues A1 and B1 but overlooked the native or enhanced activity of an insulin analogue containing a peptide linker between these residues of length similar to or exceeding that of an insulin A or B chain. Thus, the putative "closed" form of the above insulin analogues may not in fact be adequately constrained in conformation to provide significant impairment of receptor binding (relative to the modified insulin in the presence of exogenous glucose) and hence to provide useful or optimal glucose-dependent biological activity. The prescription of the above class of insulin analogues also overlooked the marked reduction in activity, irrespective of free glucose concentration, likely to arise on substitution of residues A2 or A3 ($Ile^{A2}$ or $Val^{A3}$) by other aliphatic or non-aliphatic amino acids (such as Lysine); these analogues would be expected to have negligible biological activity and thus not be useful as is long known in the art. Binding of an insulin analogue to the insulin receptor would also be impaired, but to a lesser degree, by substitution of Lysine at position A1. Also overlooked in the above class of insulin analogues is potential advantages of an alternative type of glucose-regulated conformational switch that may not only affect affinity of the analogue for the insulin receptor, but also the extent of insulin self-assembly and its rate of disassembly as might pertain to glucose-regulated pharmacokinetic properties of the subcutaneous depot.

Surprisingly, we have found that a fundamentally different class of molecule designs may optimally provide a glucose-dependent conformational switch between closed and open states of the insulin molecule without the above disadvantages. The analogues of the present invention thus contain one or more saccharide modifications at or near the C-terminal end of the B chain rather than at or near the N-terminal end of the A chain (FIGS. 3A and 3B). Further, the analogues of the present invention avoid bulky glucose-binding agents at or near residue B1 and instead employ small chemical entities (phenylboronic acid derivatives; PBA) at or near residue A1. The closed state of the present invention, tethered by an interaction (either non-covalent or covalent but reversible) between a saccharide modification (or non-saccharide analogue with similar functional groups) at or near the C-terminal end of the B chain and a small chemical entity at or near the N-terminal end of the A chain, is thus different from and unrelated to that disclosed previously. The closed state of the present invention exploits a protective hinge in the insulin molecule that opens to engage the insulin receptor. Mini-proinsulins or single-chain insulin analogues in which a short covalent tether links the C-terminus of the B chain to the N-terminus of the A chain are known in the art to exhibit very low or undetectable activity (FIG. 2). The small size of the PBA moiety attached at or near the N-terminus of the A chain and its reversible binding to a cognate PBA-binding element at or near the C-terminus of the B chain would provide a conformational switch near to the classical dimerization surface of insulin and hence make possible glucose-regulation of insulin assembly and disassembly. The essence of this invention does not depend on the specific molecular embodiment of the modification of the B chain since PBA (and PBA derivatives as a fluorophenylboronic acid) exhibit reversible covalent bonding to diol functions of both (a) diverse saccharides (differing in the number and composition of the monosaccharide subunits) and also (b) non-saccharide organic compounds that present diol functions (or α-hydroxycarboxylate as alternative PBA-binding functions) that mimic those found within a monosaccharide (FIG. 3B).

The insulin analogues of the present invention, whose biological availability (modulated by glucose-regulated rates of hexamer disassembly in the subcutaneous depot) and/or biological potency (modulated by glucose-dependent affinity for the insulin receptor) would be stronger under conditions of hyperglycemia than under conditions of hypoglycemia, would enhance the general safety, efficacy, simplicity and convenience of insulin replacement therapy.

Such an insulin analogue formulation would be compatible with multiple devices (such as insulin vials, insulin pens, and insulin pumps) and could be integrated with modifications to the insulin molecule known in the art to confer rapid-, intermediate-, or prolonged insulin action. In addition, the present glucose-regulated conformational switch in the insulin molecule, engineered between the C-terminus of the B chain and N-terminus of the A chain, could be combined with other glucose-responsive technologies (such as closed-loop systems or glucose-responsive polymers) to optimize their integrated properties. We thus envisage that the products of the present invention will benefit patients with either Type 1 or Type 2 diabetes mellitus both in Western societies and in the developing world.

SUMMARY OF THE INVENTION

It is, therefore, an aspect of the present invention to provide insulin analogues that provide glucose-responsive binding to the insulin receptor and hence glucose-regulated bioactivity. The analogues of the present investion contain two essential elements. The first element is a phenylboronic acid derivative (including a spacer element) at the α-amino group of Glycine at position A1 ($Gly^{A1}$) or optionally at either the ε-amino group of D-Lysine as an amino-acid substitution well tolerated at position A1 ($D\text{-}Lys^{A1}$) or the ε-amino group of L-Lysine as a substitution at position A4 ($L\text{-}Lys^{A4}$). Alternatively, this modification may be found near the N-terminus of the A-chain, that is, within the first 5 amino acids of the A-chain. The phenylboronic acid moiety (FIG. 4) may be modified within its aromatic ring by substitution of a hydrogen atom of a halogen atom, such as fluorine, chlorine, bromine or iodine (FIG. 5); the spacer element may contain a linear acyl chain of 1-16 carbon atoms (FIG. 6). The second element is a N-linked or O-linked monosaccharide, disaccharide, or oligosaccharide at one or near the C-terminus of the B-chain polypeptide, that is at one or more of the positions B27, B28, B29, B30, or as attached to a peptide extension of the B-chain containing one residue (B31) or two residues (B31-B32). Alternatively, a nonstandard diol-containing amino acid such as L-DOPA or D-DOPA may be substituted at any of B27-B30. Examples of O-linked saccharides are derivatives of Serine or Threonine; examples of N-linked saccharides are derivatives of Asparagine or Glutamine. Examples of monosaccharides are glucose, mannose, and N-acetyl-galactose. The overall structure of insulin analogues of the present invention is shown in schematic form in FIGS. 3A and 3B. Whereas in this scheme a general monomeric glucose-binding element attached to the A chain might be expected to require a cognate glucose or saccharide moiety attached to the B chain (FIG. 3A), the particular molecular embodiment of a monomeric glucose-binding element as a phenylboronic acid relaxes this requirement to a broad molecular diversity of diol-containing moieties (or adducts containing an α-hydroxycarboxylate group as an alternative PBA-binding function), whether a saccharide or a non-saccharide reagent (FIG. 3B). Thus, in such embodiments the N-linked or O-linked saccharide may be substituted by any organic moiety of similar molecular mass that contains a diol function that mimics the diol function of a monosaccharide and hence confers reversible PBA-binding activity (or adducts containing an α-hydroxycarboxylate group as an alternative PBA-binding function). Such non-saccharide diol-containing organic compounds span a broad range of chemical classes, including acids, alcohols, thiol reagents containing aromatic and non-aromatic scaffolds; adducts containing an α-hydroxycarboxylate group may provide an alternative PBA-binding function. Such diol-containing and alpha-hydroxycarboxylate-containing adducts in general exhibit molecular masses between 80 and 600 Dalston and in general contain 3-30 carbon atoms. Convenient modes of attachment to the B chain also span a broad range of linkages in addition to the above N-linked and O-linked saccharide derivatives described above; these additional modes of attachment include (i) the side-chain amino function of Lysine, ornithine, diaminobutyric acid, diaminopropionic acid (with main-chain chirality L or D) and (ii) the side-chain thiol function of Cysteine or homocysteine (with main-chain chirality L or D).

The analogues of the present invention may optionally contain an additional phenyboronic acid group (or halogenic derivative thereof) attached (together with a spacer element) to residue B1 as a mechanism intended to provide glucose-sensitive binding of the insulin analogue to surface lectins in the subcutaneous depot. In addition, the analogues of the present invention may optionally contain substitutions known in the art to confer rapid action (such as $Asp^{B28}$, a substitution found in insulin aspart (the active component of Novolog®); [$Lys^{B28}$, $Pro^{B29}$], pairwise substitutions found in insulin lispro (the active component of Humalog®); $Glu^{B29}$ or the combination [$Lys^{B3}$, $Glu^{B29}$] as the latter is found in insulin glulisine (the active component of Apridra®), or modifications at position B24 associated with accelerated disassembly of the insulin hexamer (e.g., substitution of $Phe^{B24}$ by Cyclohexanylalanine or by a derivative of Phenylalanine containing a single halogen substitution within the aromatic ring). Alternatively, the analogues of the present invention may optionally contain modifications known in the art to confer protracted action, such as modification of the ε-amino group of $Lys^{B29}$ by an acyl chain or acyl-glutamic acid adduct as respectively illustrated by insulin detemir (the active component of Levemir®) and insulin degludec (the active component of Tresiba®); or contain basic amino-acid substitutions or basic chain extensions designed to shift the isoelectric point (pI) to near neutrality as exemplified by the $Arg^{B31}$-$Arg^{B32}$ extension of insulin glargine (the active component of Lantus®). Analogues of the present invention designed to exhibit such a shifted pI may also contain a substitution of $Asn^{A21}$, such as by Glycine. Alanine or Serine. Analogues of the present invention may optionally also contain non-beta-branched amino-acid substitutions of $Thr^{A8}$ associated with increased affinity for the insulin receptor and/or increased thermodynamic stability as may be introduced to mitigate deleterious effects of the primary two above design elements (a phenylboronic acid derivative at or near the N-terminus of the A chain and one or more saccharide derivatives at or near the C-terminus of the B chain) on receptor-binding affinity and/or thermodynamic stability. Examples of such A8 substitutions known in the art are $His^{A8}$, $Lys^{A8}$, $Arg^{A8}$, and $Glu^{A8}$.

The two glucose-responsive mechanisms enabled by the present invention—glucose-dependent rate of insulin hexamer disassembly and glucose-dependent strength of binding to the insulin receptor—may coexist in some molecular embodiments whereas others may exhibit only one property or the other. Still other embodiments may exhibit a combination of the two properties in unequal properties. Either mechanism would be expected to confer a benefit to patients as glucose-dependent rate of insulin hexamer disassembly in the subcutaneous depot would reduce the bio-availability of the hormone under conditions of hypoglycemia whereas glucose-dependent receptor binding would reduce the potency of the hormone already in the blood stream under conditions of hypoglycemia. These two protective benefits would be expected to be independent or may even act in synergy to reduce the risk of or severity of hypoglycemic episodes.

It is also an aspect of the present invention that an innovative method of manufacture has been developed and demonstrated to the preparation of insulin analogs modified by a monomeric glucose-binding element at or near the N terminus of the A chain and modified by a saccharide or diol-containing moiety at or near the C terminus of the B chain; the latter may also containing an α-hydroxycarboxylate group as an alternative PBA-binding function. This method of manufacture exploits trypsin-mediated semi-synthesis of a pre-modified insulin fragment and a pre-modified synthetic peptide, thus simplying the purification of the final product. The insulin fragment is a des-pentapeptide[B23-B30] fragment of insulin or of a single-chain insulin precursor. The synthetic peptide contains an N-terminal glycine and is of length 6, 7, 8, 9 or 10 residues. The peptide may incorporate an N- or O-linked saccharide directly in the course of solid-phase synthesis or as a result of post-synthetic modification (FIG. 3A). The latter approach readily extends to derivitization of a basic side chain or thiol side chain by a diol-containing moiety to be used in combination with an A chain modified by phenylboronic acid as illustrated in FIG. 3B.

The insulin analogues of the present invention may exhibit an isoelectric point (pI) in the range 4.0-6.0 and thereby be amenable to pharmaceutical formulation in the pH range 6.8-7.8; alternatively, the analogues of the present invention may exhibit an isoelectric point in the range 6.8-7.8 and thereby be amenable to pharmaceutical formulation in the pH range 4.0-4.2. The latter conditions are known in the art to lead to isoelectric precipitation of such a pI-shifted insulin analogue in the subcutaneous depot as a mechanism of protracted action. An example of such a pI-shifted insulin analogue is provided by insulin glargine, in which a basic two-residue extension of the B chain ($Arg^{B31}$-$Arg^{B32}$) shifts the pI to near-neutrality and thus enables prolonged pharmacokinetic absorption from the subcutaneous depot. In general the pI of an insulin analogue may be modified through the addition of basic or acidic chain extensions, through the substitution of basic residues by neutral or acidic residues, and through the substitution of acidic residues by neutral or basic residues; in this context we define acidic residues as Aspartic Acid and Glutamic Acid, and we define basic residues as Arginine, Lysine, and under some circumstances, Histidine. We further define a "neutral" residue in relation to the net charge of the side chain at neutral pH.

It is an additional aspect of the present invention that absolute in vitro affinities of the insulin analogue for insulin receptor (isoforms IR-A and IR-B) are in the range 5-100% relative to wild-type human insulin and so unlikely to exhibit prolonged residence times in the hormone-receptor complex; such prolonged residence times are believed to be associated with enhanced risk of carcinogenesis in mammals or more rapid growth of cancer cell lines in culture. It is yet an additional aspect of the present invention that absolute in vitro affinities of the insulin analogue for the Type 1 insulin-like growth factor receptor (IGF-1R) are in the range 5-100% relative to wild-type human insulin and so unlikely either to exhibit prolonged residence times in the hormone/IGF-1R complex or to mediate IGF-IR-related mitogenesis in excess of that mediated by wild-type human insulin.

The insulin analogues of the present invention consist of two polypeptide chains that contain a novel combination of modifications in the A chain and B chain such that the analogue, in the absence of glucose or other exogenous saccharide, exhibits a reversible interaction (either covalent or non-covalent) between (a) one or more saccharide moieties or (b) one or more non-saccharide diol-containing moieties at or near the C-terminal end of the B chain to a monomeric glucose-binding moiety (optionally derived from phenylboronic acid) at or near the N-terminal end of the A chain. Examples are provided by O-linked derivatives of $Thr^{B27}$ and/or $Thr^{B30}$ by glucose, mannose, or N-acetyl-galactose and may alternatively be provided by analogous O-linked derivatives of insulin analogues containing substitution(s) of $Thr^{B27}$ and/or $Thr^{B30}$ by Serine. Further examples of monosaccarhide modifications are provided by N-linked modification of Asn or Gln when substituted at positions B26, B27, B28, B29, B30, or within a C-terminal extension of the B chain (B31 or B31-B32) up to two residues in length. Use of C-terminal extended B chains enables use of an acidic residue at B31 and/or B32 to enhance solubility and to impair cross-binding to the mitogenic IGF-1R receptor. In addition, solid-phase peptide synthesis of a B-chain fragment (as employed in trypsin-mediated semi-synthesis) containing a glycosylated residue at B30 is facilitated by such an extended peptide so that the resin-bound C-terminal residue is not glycosylated.

It is an additional aspect of the present invention that the N-linked or O-linked saccharide moiety may be replaced by any organic moiety of similar molecular mass that contains a diol function (or an α-hydroxycarboxylate group as an alternative PBA-binding function) conferring reversible binding to PBA or a PBA derivative attached at or near the N-terminus of the A chain. In some embodiments, the diol may be 3-26 carbons long. In addition or in the alternative, the molecular weight of the diol may be between 90 and 570. Examples of such non-saccharide diol-containing elements are provided by organic acids (such as gluconic acid, threonic acid, glyceric acid, galactonic acid, and dihydroxycinnamic acid), thiol-containing compounds (such as 1-thioglycerol, and 1,2,3-butanetriol4-mercapto), and amino compounds (such as (±)-3-amino-1,2-propanediol, (±)-3-amino-1,2-propanediol, and glucosamine). The thiol-containing moiety 1-thio-β-D-glucose may also be employed on disulfide linkage to a Cysteine or Homocysteine in a suitably modified B chain. Additional reagents readily obtained from commercial sources and in principle amenable to attachment to a synthetic peptide are given in Table 1; such attachment may require activation of the compound or its derivitization to provide an appropriate "chemical handle." This table is not exhaustive and is meant to provide an illustrative overview of the diversity of molecular entities (either diol-containing compounds or those containing an α-hydroxycarboxylate group), envisoned as within the scope of the present invention.

TABLE 1

| Diol- or α-hydroxycarboxylate Containing Precursors | |
|---|---|
| 1,3-benzenedimethanol | (3S,4R)-4-methyl-5-hexene-1,3-diol |
| mannitol | (3S,4R)-4-Methyl-5-hexene-2,3-diol1,3 butanediol |
| fructose | erithritol |
| sorbitol | salicylhydroxamic acid |
| Tris base | catechol |
| Fmoc-3,4-dihydroxy-L-phenylalanine | cis-1,2-cyclopentanediol |
| 2-(acetoxymethyl)-4-iodobutyl acetate | cyclohexane-1,2-diol |
| 1(1R,2S,3R,5R)-3-amino-5-(hydroxymethyl)-1,2-cyclopentanediol hydrochloride | 1,2-dihydroxybenzene |
| | dihydroxyphenylethylene glycol |
| | 2,2,4,4-tetramethyl-1,3-cyclobutanediol |

TABLE 1-continued

Diol- or α-hydroxycarboxylate Containing Precursors

| | |
|---|---|
| 2-(N-Fmoc-4-aminobutyl)-1,3-propanediol | butylboronic acid |
| 2-(4-aminobutyl)-1,3-propanediol | isosorbide |
| | N,N-dimethylsphingosine |
| 3-amino-1-,2-propandiol | sphingosine (2-amino-4-octadecene-1,3-diol) |
| 2-aminopropane-1,3-diol | tartaric acid |
| 3-mercaptopropane-1,2-diol | guaifenesin |
| 2-amino-4-pentane-1,3-diol | 5β-Androstane-3α,17α-diol-11-one-17β-carboxylic acid 3-(β-D-glucuronide) |
| N-acetyl-D-galactosamine | |
| N-acetylquinovosamine | |
| allopumiliotoxin 267A | (1S-cis)-3-bromo-3,5-cyclohexadiene-1,2-diol |
| aminoshikimic acid | |
| atorvastatin | |
| β-D-galactopyranosylamine | |
| cafestol | |
| glafenine | |
| glyceraldehyde | |
| glyceric acid | |
| glycerol 3-phosphate | |
| glycerol monostearate | |
| hydrobromide | |
| 1,2,3,4-tetrahydro isoquinoline-6,7-diol | |
| D-sphingosine | |
| cyclohexane-1,2-diol | |
| cytosine glycol | |
| 4,5-dihydroxy-2,3-pentanedione | |
| dihydroxyphenylethylene glycol | |
| dithioerythritol | |
| dithiothreitol | |
| dropropizine | |
| dyphylline | |
| flavagline FL3 | |
| floctafenine | |

Although we do not wish to be restricted by theory, we envisage that these two design elements form a reversible interaction in the absence of exogenous glucose such that the structure of the hormone is stabilized in a closed and less active conformation. It is known in the art that closure of the distance between residues B30 and A1 by chemical tethers or by short intervening peptides (or even by direct peptide bonds between $Gly^{A1}$ and either residues B28, B29 or B30) results in a marked loss of affinity of the tethered or single-chain insulin analogue for the insulin receptor. The recent co-crystal structure of insulin bound to a "micro-receptor" fragment of the ectodomain of the insulin receptor has rationalized these findings as the bound hormone exhibits partial detachment of the B24-B27 segment of the alpha-helical core of insulin. It is further known in the art that the native proximity of residues $Gly^{A1}$ and $Thr^{B30}$ reflects the positioning of the B-chain C-terminal beta-strand (residues B24-B28) relative to the central B-chain alpha-helix (residues B9-B19) such that the closed form of the insulin monomer is competent for dimerization and in turn hexamer assembly. Although not restricted by theory, we envisage that stabilization of this closed conformation by a PBA element attached at or near the N-terminus of the A chain and a complementary PBA-binding element attached at or near the C-terminus of the B chain would favor dimerization and retard the rate of insulin hexamer assembly in the subcutaneous depot. Although not restricted by theory, we further envisage that binding of an exogenous glucose molecule (or other free saccharide) to the phenylboronic acid moiety at or near the N-terminus of the A chain would prevent the tatter's interaction with O- or N-linked saccharide moieties at or near the C-terminus of the B chain, thus facilitating partial detachment of the B24-B27 segment to facilitate (a) dissociation of the insulin hexamer and dimer in the subcutaneous depot and/or (b) binding of the modified hormone to the insulin receptor in the blood stream and at target tissues.

Figure 1A:
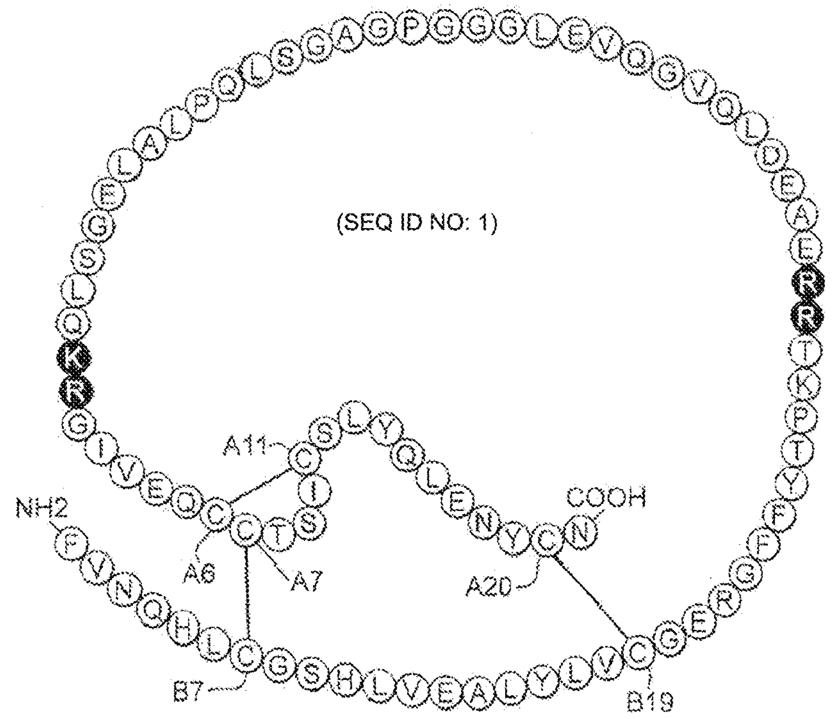
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1B:
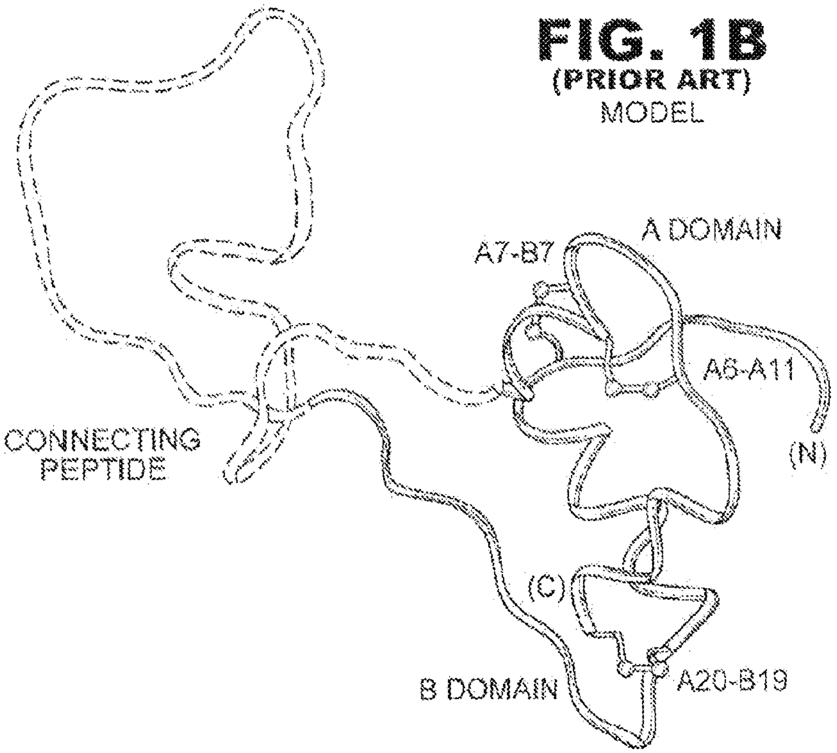
FIG. 1B is a structural model of proinsulin, consisting of an insulin-like moiety and a disordered connecting peptide (dashed line).
Figure 1C:
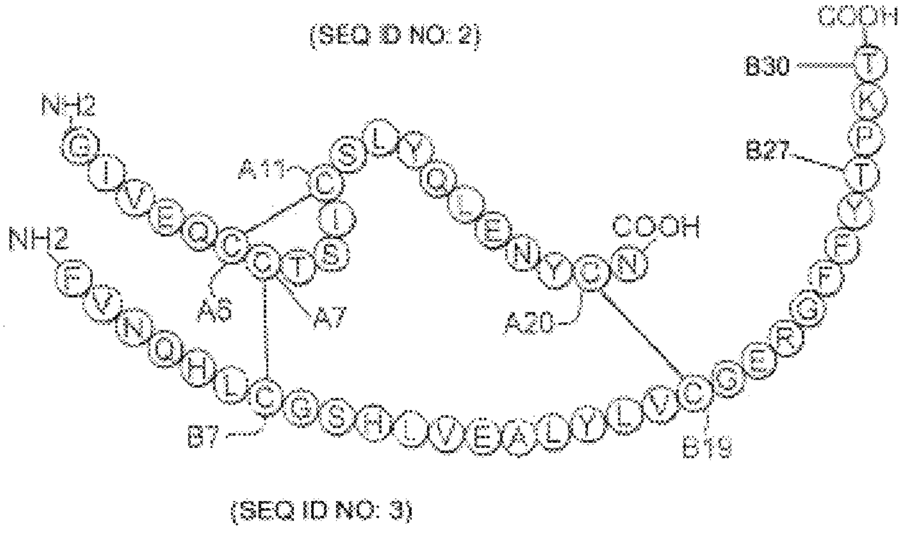
FIG. 1C is a schematic representation of the sequence of human insulin including the A-chain (SEQ ID NO: 2) and the B-chain (SEQ ID NO: 3) and indicating the position of residues B27 and B30 in the B-chain.
Figure 2:
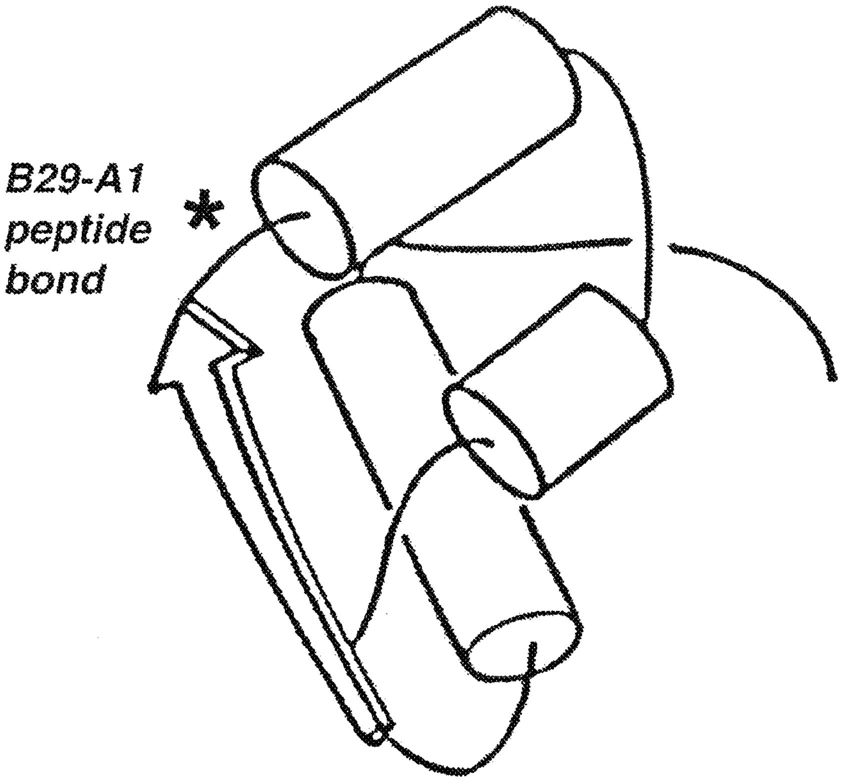
FIG. 2 is cylinder model of a mini-proinsulin (single-chain insulin) in which a peptide bond links $Lys^{B29}$ and $Gly^{A1}$; $Thr^{B30}$ has been deleted. This analogue is known in the art to have no detectable activity.
Figure 3A:
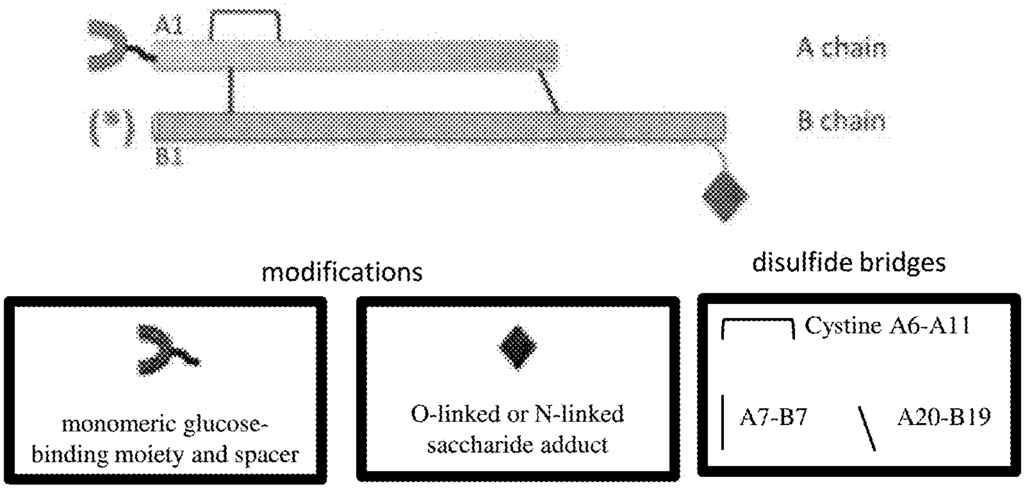

FIG. 3A is a schematic representation of the insulin molecule (top) and modifications pertaining to the present invention. The A chain is represented by the shorter horizontal cylinder and the B chain by the longer horizontal cylinder. The canonical disulfide bridges of wild-type insulin are indicated by black lines (see box at bottom right). The A chain is modified by a monomeric glucose-binding moiety and spacer at or near its N-terminus (red cup and black wavy line, respectively; see box at bottom left) and optionally at the alpha-amino group of the B chain (red asterisks in parentheses). The B chain is modified by one or more saccharide adducts at or near its C-terminus (green triangle), which may be linked to a side-chain oxygen atom of Serine or Threonine (O-linked saccharide) or linked to a side-chain nitrogen atom of Asparagine or Glutamine (N-linked saccharide). The saccharide may be a monosaccharide, disaccharide or oligosaccharide.

Figure 3B:
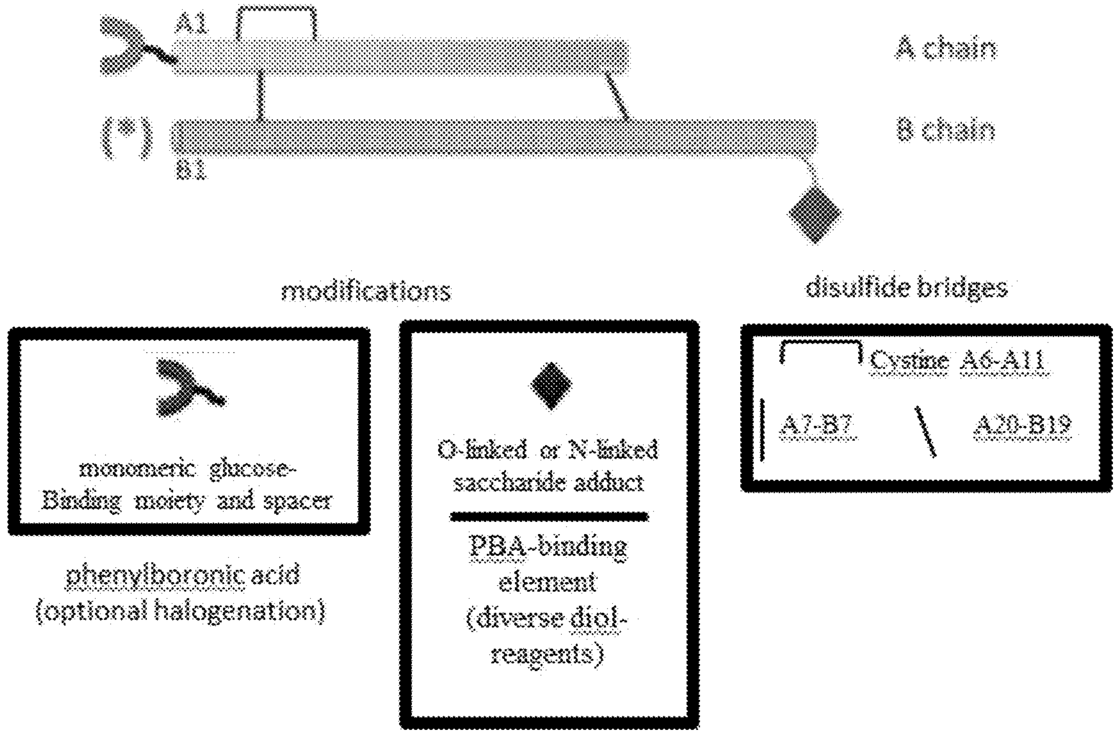

FIG. 3B is a schematic representation of a modification of the scheme shown in FIG. 3A wherein the monomeric glucose-binding element is a phenylboronic acid (with optional halogenation) whereas the matching element in the B chain may be a diol-containing moiety, whether a saccharide or as derived from a broad molecular diversity of non-saccharide diol-containing compounds, whether aromatic or non-aromatic and whether containing an amino group, carboxylate group or thiol group to facilitate attachment to an amino-acid side chain in a synthetic B-chain derived peptide.

Figure 4:
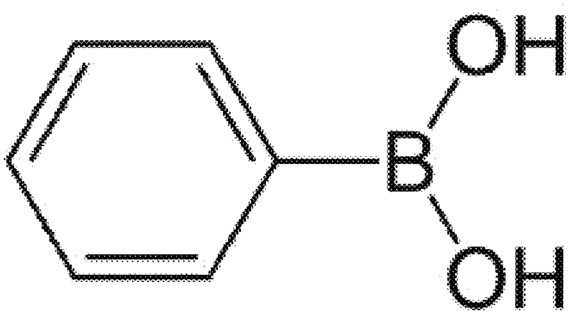

FIG. 4 is a representation of the molecular structure of phenylboronic acid.

Figure 5:
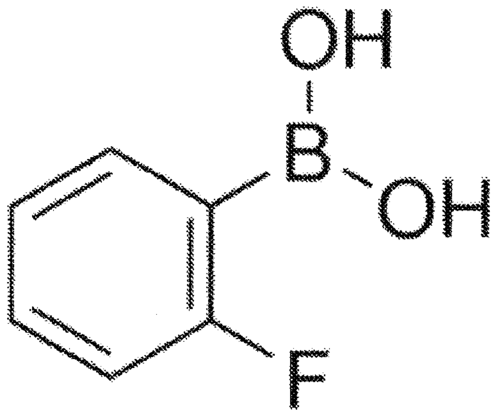

FIG. 5 is a representation of the molecular structure of a halogen-modified phenylboronic acid, in this case in which a hydrogen atom in the aromatic ring has been replaced by a fluorine atom at a position ortho to the boronic acid moiety. Halogenic modifications of the phenyl ring are known in the art to modulate the $pK_a$ of the boronic acid group.

Figure 6:
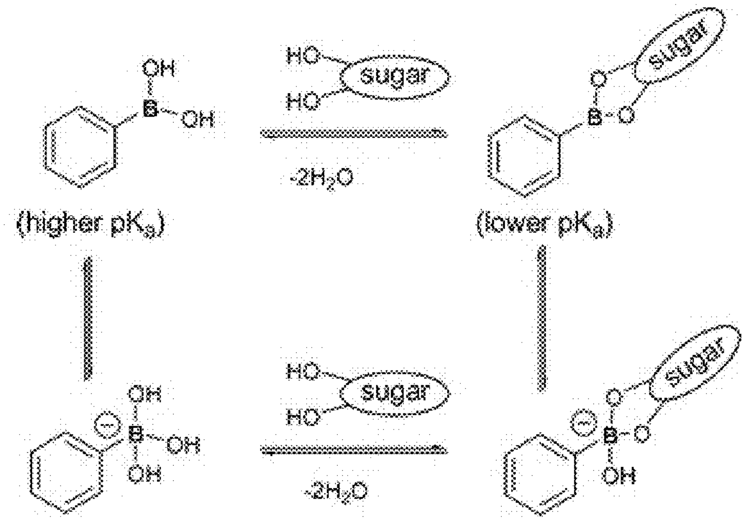

FIG. 6 is a schematic representation of the reaction scheme showing how the phenylboronic acid motiety binds to diols within saccharides. A similar reversible reaction scheme pertains to a broad class of non-saccharide chemical entities containing diol or triol functions.

Figure 7:
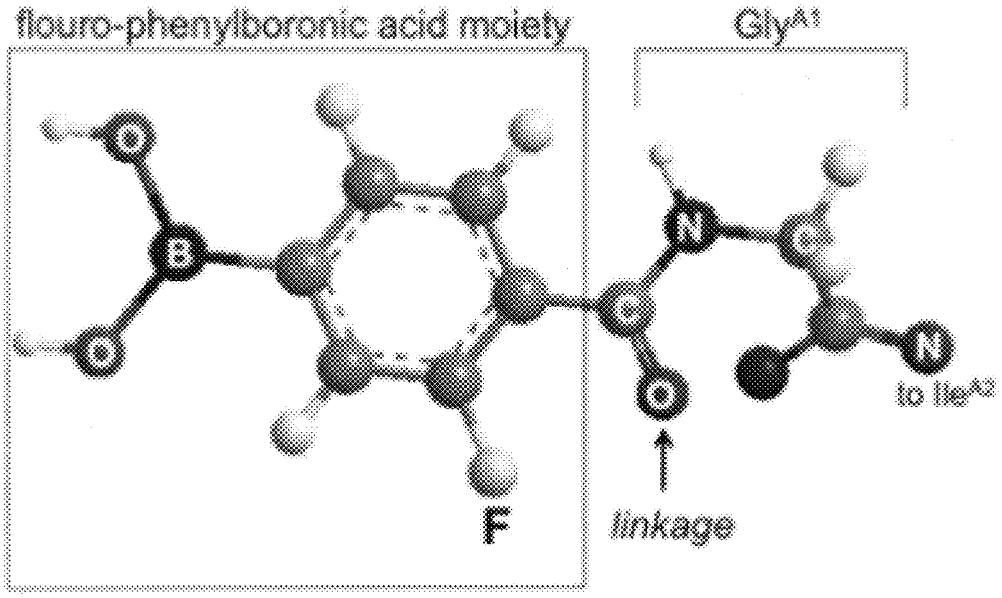

FIG. 7 is a representation of the molecular structure of the simplest linkage between a PBA moiety (left) and $Gly^{A1}$ (right) via a single carbonyl as a peptide linkage (arrow in middle). The optional fluro-derivative of the phenyl group is indicated. This chemistry was employed in our illustrative studies of examples. We envision that the PBA moiety may be separated from residue A1 by an optional acyl linker of 1-12 carbons.

Figure 8A:
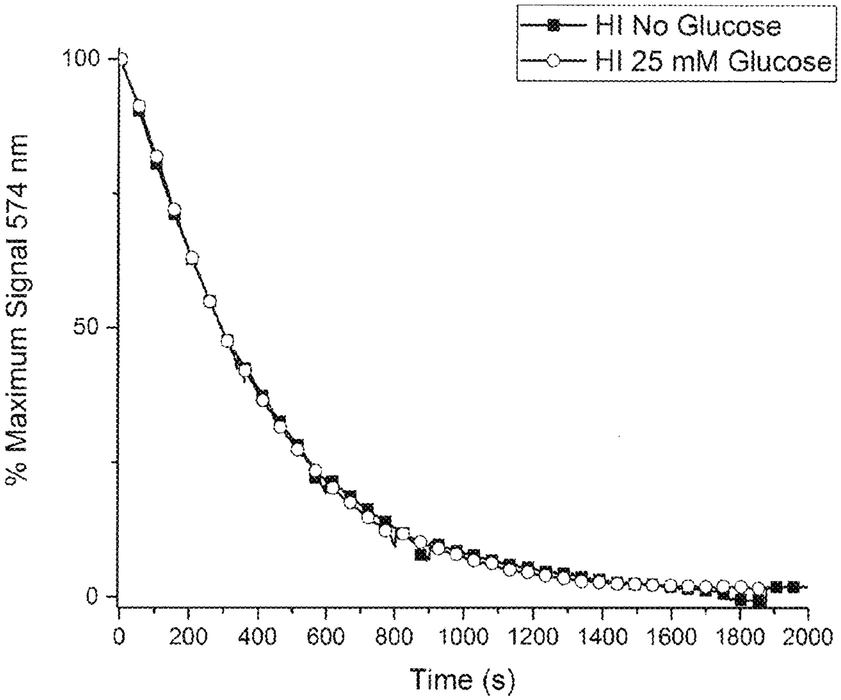

FIG. 8A is a graph of results of a control study of the rate of dissociation of wild-type human insulin in the presence or absence of glucose (25 mM) at 25° C. at pH 7.4 as probed through the EDTA cobalt-sequestration assay. No difference was observed in the rate of attenuation of the $R_6$-state-specific d-d optical band on addition of a large excess of EDTA.

Figure 8B:
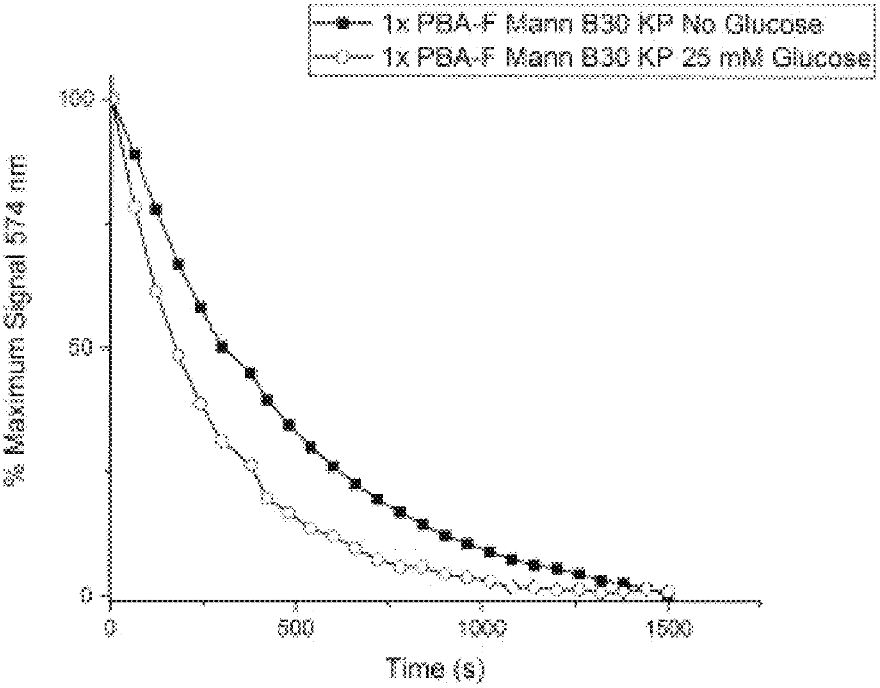

FIG. 8B is a graph showing glucose-regulated rates of dissociation of hexamer disassembly in a representative analog of the present invention (in which $Gly^{A1}$ was derivatized by flouro-phenylboronic acid (SEQ ID NO: 51) and $Thr^{B30}$ contained an O-linked mannosyl modification Table 2). The analogue contained the paired $Lys^{B28}$-$Pro^{B29}$ substitutions of insulin lispro (Humalog) and a $Glu^{B31}$-$Glu^{B32}$ C-terminal extension of the B chain (SEQ ID NO: 16).

Figure 8C:
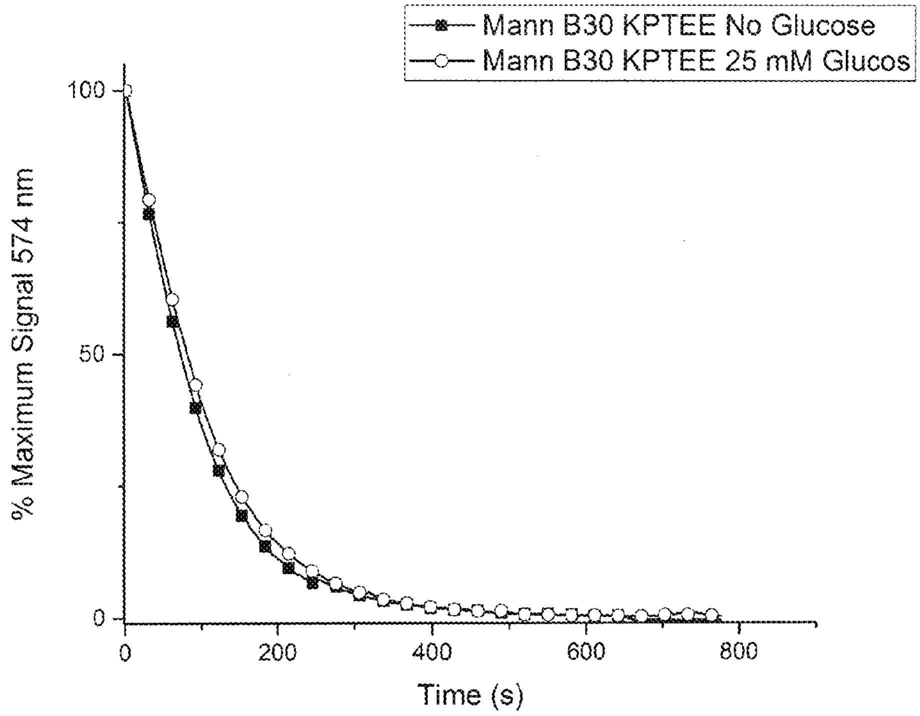

FIG. 8C is a graph showing results of a control cobalt-sequestration study of an analogue lacking a PBA modification of residue A1 (or elsewhere) but otherwise identical to the analogue described in panel B, including with an O-linked mannose attached to $Thr^{B30}$. This control analogue exhibits little or no difference in rate of disassembly in the presence or absence of 25 mM glucose; the small difference between curves may be experimental error or may represent a small unfavorable retardation of disassembly under conditions of hyperglycemia (i.e., opposite to what would be beneficial to a patients with diabetes mellitus).

Figure 9:
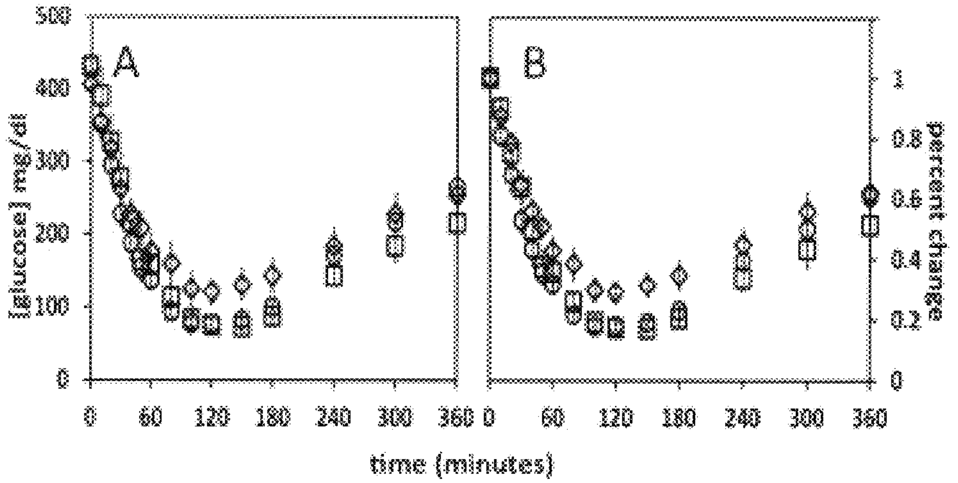

FIG. 9 provides a pair of graphs of results of a rat study of the potency of selected insulin analogs on intravenous bolus injection in a rat model of diabetes mellitus. The data provide a comparison of the biological activities of an insulin analog of the present invention (diamonds; N=6 studies of mannose-$Thr^{B30}$ in combination with fluoro-PBA attached to the α-amino group of $Gly^{A1}$ in a variant B chain containing $Lys^{B28}$ and $Pro^{B29}$ together with C-terminal extension $Glu^{B31}$ and $Glu^{B32}$) versus a similar analogue lacking the PBA modification at A1 (circles; N=5) and insulin lispro (squares with N=5; insulin lispro is the active component of Humalog). In panel A the data are plotted in relation to the absolute blood-glucose concentrations (vertical axis in mg/dl) whereas in panel B the data are plotted relative to the initial values of the blood-glucose concentrations (defined as 1.0). The study was performed in male Lewis rats rendered diabetic by stretozotocin at a dose corresponding to 20-μg protein per 300-gram rat.

DETAILED DESCRIPTION OF THE INVENTION

The present invention is directed toward an insulin analogue that provides enhanced in vivo glycemic control through glucose-dependent rates of insulin hexamer disassembly in the subcutaneous depot and/or glucose-dependent binding to the insulin receptor in the blood stream and at target tissues. Six novel insulin analogues were prepared as listed in Table 2. Each employs fluoro-phenylboronic acid as the glucose-sensing element. The chemical linkage between the fluoro-PBA moiety and the α-amino group of $Gly^{A1}$ is illustrated in FIG. 7; the corresponding linkage was employed in analogues with simultaneous fluoro-PBA adduct at the α-amino group of $Phe^{B1}$ (not shown).

Two analogues contain one such adduct (at the α-amino group of the A chain; Table 2A) and three analogues contain two such adducts (at the α-amino groups of both the A- and B chains; Table 2B). The protocol for derivitization of an insulin fragment by an activare FPA reagent is provided below. These analogues contained O-linked α-D-mannopyranoside (mannose-$O^{β}$-Thr) or α-D-glucopyranoside (glucose-$O^{β}$-Thr) at positions of naturally occurring Threonine in human insulin (residues B27 and/or B30). Predicted molecular masses were in each case verified by mass spectrometry. The mannose-containing insulin analogues exhibited cobalt $R_6$ hexamer assembly properties similar to those of WT insulin (but with different disassembly kinetics; below) as illustrated in FIG. 8. The mannose-containing insulin analogues exhibited biological activities on IV bolus injection into male Lewis rats rendered diabetic by steptozotocin similar to that of insulin lispro, the active component of Humalog® (Eli Lilly) as illustrated in FIG. 9.

TABLE 2

| Insulin Analogues | |
|---|---|
| A. Single PBA Modification ($Gly^{A1}$) | B. Dual PBA Modification ($Gly^{A1}$ and $Phe^{B1}$) |
| Mannose-$Thr^{B30}$-$Lys^{B28}$-$Pro^{B29}$-$Glu^{B31}$-$Glu^{B32}$ | Mannose-$Thr^{B30}$-$Lys^{B28}$-$Pro^{B29}$-$Glu^{B31}$-$Glu^{B32}$ |
| | Mannose-$Thr^{B30}$-$Orn^{B29}$-$Glu^{B31}$-$Glu^{B32}$ |
| Glucose-$Thr^{B27}$-Glucose-$Thr^{B27}$-$Lys^{B28}$-$Pro^{B29}$-$Glu^{B31}$-$Glu^{B32}$ | Glucose-Thr-$^{B27}$-Glucose-$Thr^{B27}$-$Lys^{B28}$-$Pro^{B29}$-$Glu^{B31}$-$Glu^{B32}$ |

To demonstrate that representative analogues of the present invention retain high affinity for the insulin receptor, such affinities were measured by an in vitro competitive-displacement scintillation proximity assay (below). A standard control sample was provided by $Orn^{B29}$-insulin, whose activity is indistinguishable from that of wild-type insulin. The affinity of the insulin analogue containing O-linked mannose-$Thr^{B30}$ in the context of a [Glu, Glu]-extended lispro B chain i.e., with substitutions $Lys^{B28}$ and $Pro^{B29}$ and with C-terminal extension $Glu^{B31}$ and $Glu^{B32}$) was observed to be (i) in the range 50-75% (relative to $Orn^{B29}$-insulin) in the presence a fluoro-PBA adduct attached to the α-amino group of $Gly^{A1}$ and (ii) in the range 10-30% (relative to $Orn^{B29}$-insulin) in the presence fluoro-PBA adducts attached to the α-amino groups of both $Gly^{A1}$ and $Phe^{B1}$. We attribute these modest reductions in affinity to the unfavorable effects of the A1 and B1 adducts as is known in the art. We and others have previously disclosed that the lispro substitutions ($Lys^{B28}$ and $Pro^{B29}$) and C-terminal extension $Glu^{B31}$ and $Glu^{B32}$ have negligible effects on the affinity of otherwise diverse insulin analogues for the isolated insulin receptor; modification of $Thr^{B30}$ by an O-linked mannosyl moiety is likewise well tolerated.

Glucose-responsive rates of disassembly were investigated using a spectroscopy assay in which the visible absorption spectrum of a cobalt ($Co^{2+}$)-substituted insulin hexamer was obtained in the presence of phenol as an $R_6$ hexamer. This assay (as described in Richard, J. P. et al. ("Self-association properties of monomeric insulin analogs under formulation conditions." *Pharm. Res.* 15:1434-41; 1998.) exploits the R-state-specific tetrahedral coordination of the metal ion, which gives rise to a blue absorption band.

This band arises front the unfilled d-shell electrons of the cobalt ion and is a specific signature of a tetrahedral coordination environment. Addition of a large excess of the chelating agent ethylene-diamine-tetra-acetic acid (EDTA)

leads to progressive sequestration of the metal ion (in a colorless octahedral complex) and so provides a rapid and convenient probe of the kinetics of hexamer disassembly. Wild-type insulin exhibits the same rate of loss of the R-state-specific d-d signal in the presence of absence of glucose at a contration of 25 mM (FIG. 8A). By contrast, the analogue listed in Table 2A (Mannose-Thr$^{B30}$-Lys$^{B28}$-Pro$^{B29}$-Glu$^{B31}$-Glu$^{B32}$) exhibits a marked acceleration of disassembly under conditions of hyperglycemia (FIG. 8B). Such glucose-regulated disassembly does not occur in the presence of the mannose adduct in the B chain but absence of the PBA adduct at the N-terminus of the A chain (FIG. 8C).

It is a feature of the present invention that when the blood glucose concentration is within or below the normal range, the claimed insulin analogues exhibit low affinities for the insulin receptor relative to wild-type insulin. Although not wishing to be constrained by theory, we envisage that this reduction in affinity is a consequence of a reversible interaction between a saccharide modification at or near the C-terminal end of the B chain and a phenylboronic acid derivative attached to the A chain at or near its N-terminal end. Such a covalent yet reversible interaction would "close" the conformation of the B chain C-terminal beta-strand (residues B24-B28) and thus hinder binding to the insulin receptor, which requires partial detachment of this beta-strand from the alpha-helical core of the insulin molecule. It is a feature of the present invention that the glycemic potency of the claimed insulin analogues is restored to levels similar to that of wild-type insulin when the blood-glucose concentration is above the normal range due to competitive displacement of the A-chain-linked phenylboronic acid derivative from the B-chain-linked saccharide motiety or moieties by the excess of exogenous glucose in solution. We envisage that receptor-binding affinities in the presence of glucose at a concentration >200 mg/ml that are in the range 5-100% would be sufficient to confer such native or near-native glycemic potency in an animal with diabetes mellitus. It is an additional feature of the present invention that these modifications are also likely to reduce the tendency of insulin to undergo fibrillation at or above room temperature and to attenuate the mitogenicity of insulin, a. distinct signaling pathway that is undesirable from the perspective of cancer risk and cancer growth.

It is also envisioned that insulin analogues may be made with A- and B chain sequences derived from animal insulins, such as porcine, bovine, equine, and canine insulins, by way of non-limiting examples, so long as the A-chain is modified by a phenylboronic acid derivative at or near its N-terminus, and one or more amino-acid side chains at or near the C-terminus of the B chain are modified by O-linked or N-linked monosaccharides, disaccharides or oligosaccharides. Such variant B chains derived from human insulin or animal insulins may optionally contain a C-terminal dipeptide extension (with respective residue positions designated B31 and B32) wherein at least one of these C-terminal extended residues is a modified amino acid containing an O-linked or N-linked saccharide. In addition or in the alternative, the insulin analogue of the present invention may contain a deletion of residues B1-B3 or may be combined with a variant B chain lacking Proline at position B28 (e.g., [Lys$^{B28}$, Pro$^{B29}$] as in Humalog; or Asp$^{B28}$ or Glu$^{B28}$ in combination with Lysine or Proline at position B29) or containing Glutamic Acid at position B29. At position A13 Leucine may optionally be substituted by Tryptophan, and at position A14 Tyrosine may optionally be substituted by Glutamic Acid.

It is further envisioned that the insulin analogues of the present invention may be derived from Lys-directed proteolysis of a precursor polypeptide in yeast biosynthesis in *Pichia pastoris, Saccharomyces cerevisciae*, or other yeast expression species or strains. Such strains may be engineered to insert halogen-modified Phenylalanine at position B24 by means of an engineered tRNA synthetase and orthogonal nonsense suppression. The B-domain of the insulin analogues of the present invention may optionally contain non-standard substitutions, such as D-amino-acids at positions B20 and/or B23 (intended to augment thermodynamic stability, receptor-binding affinity, and resistance to fibrillation). The halogenic modification at position B24 may be at the 2-ring position of Phe$^{B24}$ (i.e., ortha-F-Phe$^{B24}$, ortho-Cl-Phe$^{B24}$, or ortho-Br-Phe$^{B24}$. Optionally, the analogues may contain iodo-substitutions within the aromatic ring of Tyr$^{B16}$ and/or Tyr$^{B26}$ (3-mono-iodo-Tyr or [3,5]-di-iodo-Tyr); intended to augment thermodynamic stability and receptor-binding activity). It is also envisioned that Thr$^{B27}$, Thr$^{B30}$, or one or more Serine residues in the C-domain may be modified, singly or in combination, by a monosaccaride adduct; examples are provided by O-linked N-acetyl-β-D-galactopyranoside (designated GalNAc-O$^{β}$-Ser or GalNAc-O$^{β}$-Thr), O-linked α-D-mannopyranoside (mannose-O$^{β}$-Ser or mannose-O$^{β}$-Thr), and/or α-D-glucopyranoside (glucose-O$^{β}$-Ser or glucose-O$^{β}$-Thr).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Acidic amino acids are Aspartic acid (Asp or D) and Glutamic acid (Glu or E). Introduction of basic amino-acid substitutions (including Lysine (Lys or K), Arginine (Arg or R) and Histidine (His or H)) are not preferred in order to maintain the enhanced net negative charge of this class of analogues. Unless noted otherwise or wherever obvious from the context, the amino acids noted herein should be considered to be L-amino acids. Standard amino acids may also be substituted by non-standard amino acids belonging to the same chemical class.

The insulin analogues of the present invention include (but are not restricted to) insulin analogues whose variant B chain conforms to the polypeptide sequences given in SEQ ID NOs 7-50 below and whose variant A chain conforms to the polypeptide sequences given in SEQ ID NOs 51-53. It is understood that the variant B chains of the present invention may also include deletion of residue B1, deletion of residues B1 and B2, or deletion of residues B1-B3 such that the neo-C-terminal α-amino group may optionally be modified by a phenylboronic acid derivative. The amino-acid sequence of human proinsulin is provided, for comparative purposes, as SEQ ID NO: 1. The amino-acid sequence of the human A chain is provided, for comparative purposes, as SEQ ID NO: 2, The amino-acid sequences of the human B chain and B-chain analogues known in the art are provided, for comparative purposes, as SEQ ID NO: 3-6.

The amino-acid sequence of human proinsulin is provided, for comparative purposes, as SEQ ID NO: 1.

(human proinsulin)

SEQ ID NO: 1

Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr-Arg-Arg-Glu-Ala-Glu-Asp-

Leu-Gln-Val-Gly-Gln-Val-Glu-Leu-Gly-Gly-Gly-Pro-

Gly-Ala-Gly-Ser-Leu-Gln-Pro-Leu-Ala-Leu-Glu-Gly-

Ser-Leu-Gln-Lys-Arg-Gly-Ile-Val-Glu-Gln-Cys-Cys-

Thr-Ser-Ile-Cys-Ser-Leu-Tyr-Gln-Leu-Glu-Asn-Tyr-

Cys-Asn

The amino-acid sequence of the A chain of human insulin is provided as SEQ ID NO: 2.

(human A chain)

SEQ ID NO: 2

Gly-Ile-Val-Glu-Gln-Cys-Cys-Thr-Ser-Ile-Cys-Ser-

Leu-Tyr-Gln-Leu-Glu-Asn-Tyr-Cys-Asn

The amino-acid sequence of the B chain of human insulin is provided as SEQ ID NO: 3.

(human B chain)

SEQ ID NO: 3

Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Lys-Thr

The amino-acid sequence of the "KP" B chain of prandial insulin analogue KP-insulin contains substitutions $Pro^{B28}$→Lys and $Lys^{B29}$→Pro as provided in SEQ ID NO: 4.

SEQ ID NO: 4

Phe-Val- Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Try-Thr-Lys-Pro-Thr

The 32-residue amino-acid sequence of an extended "KP" B chain of prandial insulin analogue KP-insulin is provided in SEQ ID NO: 5.

SEQ ID NO: 5

Phe-Val- Glu-Gln-His-Leu-Cys-Gly-Ser-His-Leu-Val-

Glu-Ala-Leu-Tyr-Leu-Val-Cys-Gly-Glu-Arg-Gly-Phe-

Phe-Try-Thr-Lys-Pro-Thr-Glu-Glu

The 30-residue amino-acid sequence of a variant B chain modified to contain Ornithine at position B29 is provided in SEQ ID NO: 6.

SEQ ID NO: 6

-continued

Phe-Val- Glu-Gln-His-Leu-Cys-Gly-Ser-$Xaa_4$Leu-Val-

Glu-Ala-Leu-Tyr-Leu-Val-Cys-Gly-Glu-Arg-Gly-Phe-

Phe-Try-Thr-Pro-Orn-Thr

The amino-acid sequence of a variant B chain modified by O-linked glycosylation at residue B27 while retaining $Pro^{B28}$ is provided in SEQ ID NO: 7.

SEQ ID NO: 7

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-$Xaa_3$-Pro-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $O^{β}$-$Thr^{B27}$-linked or $O^{β}$-$Ser^{B27}$-linked monosaccaride pyranoside selected from a group consisting of α-D-mannopyranoside, α-D-glucopyranoside, or N-acetyl-β-D-galactopyranoside, or where $Xaa_3$ is an $O^{β}$-$Thr^{B27}$-linked or $O^{β}$-$Ser^{B27}$-linked disaccharide containing one or more of the above monosaccharide subunits; where $Xaa_4$ is Lysine, Ornithine, Arginine, di-amino-butyric acid, di-amino-propionic acid, Norleucine, aminobutyric acid, aminopropionic acid, Alanine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by O-linked glycosylation at residue B27 with alternative placement of Proline at position B29 is provided in SEQ ID NO: 8.

SEQ ID NO: 8

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-$Xaa_3$-$Xaa_4$-Pro-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $O^{β}$-$Thr^{B27}$-linked or $O^{β}$-$Ser^{B27}$-linked monosaccaride pyranoside selected from a group consisting of α-D-mannopyranoside, α-D-glucopyranoside, or N-acetyl-β-D-galactopyranoside, or where $Xaa_3$ is an $O^{β}$-$Thr^{B27}$-linked of $O^{β}$-$Ser^{B27}$-linked disaccharide containing one or more of the above monosaccharide subunits; where $Xaa_4$ is Lysine, Arginine, Ornithine, di-aminobutyric acid, di-aminopropionic acid, Alanine, Aspartic Acid, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B27 while retaining $Pro^{B28}$ is provided in SEQ ID NO: 9.

```
                                         SEQ ID NO: 9
Xaa1-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa2-Phe-Tyr-Xaa3-Pro-Xaa4-Thr-Xaa5-Xaa6
```

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $N^{\beta}$-$Asn^{B27}$-linked or $N^{\gamma}$-$Gln^{B27}$-linked monosaccaride pyranoside selected from a group consisting of α-D-mannopyranoside, α-D-glucopyranoside, or N-acetyl-β-D-galactopyranoside or where $Xaa_3$ is an $N^{\beta}$-$Asn^{B27}$-linked or $N^{\gamma}$-$Gln^{B27}$-linked disaccharide containing one or more of the above monosaccharide subunits; where $Xaa_4$ is Lysine, Ornithine, Arginine, di-amino-butyric acid, di-amino-propionic acid, Norleucine, aminobutyric acid, aminopropionic acid, Alanine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B27 with alternative placement of Proline at position B29 is provided in SEQ ID NO: 10.

```
                                         SEQ ID NO: 10
Xaa1-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa2-Phe-Tyr-Xaa3-Xaa4-Pro-Thr-Xaa5-Xaa6
```

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $N^{\beta}$-$Asn^{B27}$-linked or $N^{\gamma}$-$Gln^{B27}$-linked monosaccaride pyranoside selected from a group consisting of α-D-mannopyranoside, α-D-glucopyranoside, or N-acetyl-β-D-galactopyranoside, or where $Xaa_3$ is an $N^{\beta}$-$Asn^{B27}$-linked or $N^{\gamma}$-$Gln^{B27}$-linked disaccharide containing one or more of the above monosaccharide subunits; where $Xaa_4$ is Lysine, Arginine, Ornithine, di-aminobutyric acid, di-aminopropionic acid, Alanine, Aspartic Acid, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by a diol-containing reagent at a basic residue at position B27 while retaining $Pro^{B28}$ is provided in SEQ ID NO: 11.

```
                                         SEQ ID NO: 11
Xaa1-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa2-Phe-Tyr-Xaa3-Pro-Xaa4-Thr-Xaa5-Xaa6
```

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Lysine, Ornithine, di-aminobutyric acid or di-aminopropionic acid whose side chain amino group is linked to a diol-containing reagent; where $Xaa_4$ is an Arginine, Alanine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by diol-containing reagent at a basic residue at position B27 with alternative placement of Proline at position B29 is provided in SEQ ID NO: 12.

```
                                         SEQ ID NO: 12
Xaa1-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa2-Phe-Tyr-Xaa3-Xaa4-Pro-Thr-Xaa5-Xaa6
```

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Lysine, Ornithine, di-aminobutyric acid or di-aminopropionic acid whose side chain amino group is linked to a diol-containing reagent; where $Xaa_4$ is Arginine, Alanine, Aspartic Acid, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by a diol-containing reagent at a sulfur-containing residue at position B27 while retaining $Pro^{B28}$ is provided in SEQ ID NO: 13.

```
                                         SEQ ID NO: 13
Xaa1-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa2-Phe-Tyr-Xaa3-Pro-Xaa4-Thr-Xaa5-Xaa6
```

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Cysteine or Homocysteine whose side-chain sulfur atom is linked to a diol-containing reagent; where $Xaa_4$ is an Arginine, di-amino-butyric acid, di-amino-propionic acid, Norleucine, aminobutyric acid, aminopropionic acid, Alanine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by diol-containing reagent at a sulfur-containing residue at position B27 with alternative placement of Prolific at position B29 is provided in SEQ ID NO: 14.

SEQ ID NO: 14

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-$Xaa_3$-$Xaa_4$-Pro-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$;

where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Cysteine or Homocysteine whose side-chain sulfur atom is linked to a diol-containing reagent; where $Xaa_4$ is Arginine, Ornithine, di-aminobutyric acid, di-aminopropionic acid, Alanine, Aspartic Acid, or Glutamic Acid; and where $Xaa_5$-$Xaa_6$, represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by O-linked glycosylation at residue B30 while retaining $Pro^{B28}$ is provided in SEQ ID NO: 15.

SEQ ID NO: 15

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-promo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; $Xaa_4$ is $O^\beta$-$Thr^{B30}$-linked or $O^\beta$-$Ser^{B30}$-linked monosaccharide pyranoside selected from a group consisting of α-D-mannopyranoside, α-D-glucopyranoside, or N-acetyl-β-D-galactopyranoside, or where $Xaa_4$ is an $O^\beta$-$Thr^{B30}$-linked or $O^\beta$-$Ser^{B30}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by O-linked glycosylation at residue B30 with alternative placement of Proline at position B29 is provided in SEQ NO: 16.

SEQ ID NO: 16

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-$Xaa_4$-$Xaa_5$-$Xaa_6$

Where $Xaa_1$ is either the native α-amino group of Phe or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Arginine, Ornithine, di-aminobutyric acid, di-aminopropionic acid, Alanine, Aspartic Acid, or Glutamic Acid; $Xaa_4$ is $O^\beta$-$Thr^{B30}$-linked or $O^\beta$-$Ser^{B30}$-linked monosaccharide pyranoside selected from a group consisting of α-D-mannopyranoside, α-D-glucopyranoside, or N-acetyl-β-D-galactopyranoside, or where $Xaa_4$ is an $O^\beta$-$Thr^{B30}$-linked or $O^\beta$-$Ser^{B30}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B30 while retaining $Pro^{B28}$ is provided in SEQ ID NO: 17.

SEQ ID NO: 17

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; where $Xaa_4$ is an $N^\beta$-$Asn^{B30}$-linked or $N^\gamma$-$Gln^{B30}$-linked monosaccharide pyranoside selected from a group consisting of α-D-mannopyranoside, α-D-glucopyranoside, or N-acetyl-β-D-galactopyranoside, or where $Xaa_4$ is an $N^\beta$-$Asn^{B30}$-linked or $N^\gamma$-$Gln^{B30}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B30 with alternative placement of Proline at position B29 is provided in SEQ ID NO: 18.

SEQ ID NO: 18

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Arginine, Ornithine, di-aminobutyric acid, di-aminopropionic acid, Alanine, Aspartic Acid, or Glutamic Acid: where $Xaa_4$ is an $N^{\beta}$-$Asn^{B30}$-linked or $N^{\gamma}$-$Gln^{B30}$-linked monosaccharide pyranoside selected from a group consisting of α-D-mannopyranoside, α-D-glucopyranoside, or N-acetyl-β-D-galactopyranoside, or where $Xaa_4$ is an $N^{\beta}$-$Asn^{B30}$-linked or $N^{\gamma}$-$Gln^{B30}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by a diol-containing reagent at a basic residue at position B30 while retaining $Pro^{B28}$ is provided in SEQ ID NO: 19.

SEQ ID NO: 19

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid or Glutamic Acid; where $Xaa_4$ is a derivative of the D or L stereoisomer of Lysine, Ornithine, di-aminobutyric acid or di-aminopropionic acid whose side chain amino group is linked to a diol-containing reagent; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by diol-containing reagent at a basic residue at position B30 with alternative placement of Proline at position B29 is provided in SEQ ID NO: 20.

SEQ ID NO: 20

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid, or Glutamic Acid; where $Xaa_4$ is a derivative of the D or L stereoisomer of Lysine, Ornithine, di-aminobutyric acid or di-aminopropionic acid whose side chain amino group is linked to a diol-containing reagent; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by a diol-containing reagent at a sulfur-containing residue at position B30 while retaining $Pro^{B28}$ is provided in SEQ ID NO: 21.

SEQ ID NO: 21

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid or Glutamic Acid; where $Xaa_4$ is a derivative of the D or L stereoisomer of Cysteine or Homocysteine whose side-chain sulfur atom is linked to a diol-containing reagent; and where $Xaa_5$-$Xaa_6$ represent optional one- or two-residue extensions of the B chain where $Xaa_5$ (if elected to be present) may be Glu, Gln, Ala, or Ser and where $Xaa_5$-$Xaa_6$ (if elected to be present) is drawn from the same set of amino acids such that at least one extended position is Glutamic Acid.

The amino-acid sequence of a variant B chain modified by diol-containing reagent at a sulfur-containing residue at position B30 with alternative placement of Proline at position B29 is provided in SEQ ID NO: 22.

SEQ ID NO: 22

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-$Xaa_4$-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid, or Glutamic Acid; where $Xaa_4$ is a derivative of the D or L stereoisomer of Cysteine or Homocysteine whose side-chain sulfur atom is linked to a diol-containing reagent; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by O-linked glycosylation at residue B31 while retaining $Pro^{B28}$ is provided in SEQ ID NO: 23.

SEQ ID NO: 23

$Xaa_1$-Phe-Val-Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; where $Xaa_4$ is an $O^{\beta}$-$Thr^{B31}$-linked linked or $O^{\beta}$-$Ser^{B31}$-linked monosaccaride pyranoside selected from a group consisting of α-D-mannopyranoside, α-D-glucopyranoside, or N-acetyl-β-D-galactopyranoside, or where $Xaa_4$ is an $O^{\beta}$-$Thr^{B31}$-linked or $O^{\beta}$-$Ser^{B31}$-linked disaccharide containing one or more of the above monosaccharide subunits; and where $Xaa_5$ represent Glu, Gln, Gly, Ala, or Ser.

The amino-acid sequence of a variant B chain modified by O-linked glycosylation at residue B31 with alternative placement of Proline at position B29 is provided in SEQ ID NO: 24.

SEQ ID NO: 24

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_4$-Pro-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Arginine, Ornithine, di-aminobutyric acid, di-aminopropionic acid, Alanine, Aspartic Acid, or Glutamic Acid; where $Xaa_4$ is an $N^{\beta}$-$Asn^{B31}$-linked or $N^{\gamma}$-$Gln^{B31}$-linked monosaccharide pyranoside selected from a group consisting of α-D-mannopyranoside, α-D-glucopyranoside, or N-acetyl-β-D-galactopyranoside, or where $Xaa_4$ is an $N^{\beta}$-$Asn^{B31}$-linked or $N^{\gamma}$-$Gln^{B31}$-linked disaccharide containing one or more of the above monosaccharide subunits; and $Xaa_5$ is Glu, Gln, Gly, Ala, or Ser.

The amino-acid sequence of a variant B chain modified by N-linked glycosylation at residue B31 while retaining $Pro^{B28}$ is provided in SEQ ID NO: 25.

SEQ ID NO: 25

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; where $Xaa_4$ is an $N^{\beta}$-$Asn^{B31}$-linked or $N^{\gamma}$-$Gln^{B31}$-linked monosaccaride pyranoside selected from a group consisting of α-D-mannopyranoside, α-D-glucopyranoside, or N-acetyl-β-D-galactopyranoside, or where $Xaa_4$ is an $N^{\beta}$-$Asn^{B31}$-linked or $N^{\gamma}$-$Gln^{B31}$-linked disaccharide containing one or more of the above monosaccharide subunits; and where $Xaa_5$ is Glu, Gln, Gly, Ala, or Ser.

The amino-acid sequence of a variant B chain modified by N-linked glycosylation at residue B31 with alternative placement of Proline at position B29 is provided in SEQ ID NO: 26.

SEQ ID NO: 26

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-aminobutyric acid, di-amino-propionic acid, Norleucine, aminobutyric acid, aminopropionic acid, Alanine, or Glutamic Acid; where $Xaa_4$ is an $N^{\beta}$-$Asn^{B31}$-linked or $N^{\gamma}$-$Gln^{B31}$-linked monosaccaride pyranoside selected from a group consisting of α-D-mannopyranoside, α-D-glucopyranoside, or N-acetyl-β-D-galactopyranoside, or where $Xaa_4$ is an $N^{\beta}$-$Asn^{B31}$-linked or $N^{\gamma}$-$Gln^{B31}$-linked disaccharide containing one or more of the above monosaccharide subunits; and where $Xaa_5$ is Glu, Gln, Ala, or Ser.

The amino-acid sequence of a variant B chain modified by a diol-containing reagent at residue B31 while retaining $Pro^{B28}$ is provided in SEQ ID NO: 27.

SEQ ID NO: 27
$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; where $Xaa_4$ is Alanine, Arginine, Aspartic Acid or Glutamic Acid; where $Xaa_5$ is a derivative of the D or L stereoisomer of Lysine, Ornithine, di-aminobutyric acid or di-aminopropionic acid whose side chain amino group is linked to a diol-containing reagent; and where $Xaa_5$ (if elected to be present) is optionally Glu, Gln, Gly, Ala, or Ser.

The amino-acid sequence of a variant B chain modified by diol-containing reagent at residue B31 with alternative placement of Proline at position B29 is provided in SEQ ID NO: 28.

SEQ ID NO: 28
$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid, or Glutamic Acid; where $Xaa_4$ is Alanine, Arginine, Aspartic Acid or Glutamic Acid; where $Xaa_5$ is a derivative of the D or L stereoisomer of Lysine, Ornithine, di-aminobutyric acid or di-aminopropionic acid whose side chain amino group is linked to a diol-containing reagent; and where $Xaa_5$ (if elected to be present) is optionally Glu, Gln, Gly, Ala, or Ser.

The amino-acid sequence of a variant B chain modified by a diol-containing reagent at a basic residue at position B32 while retaining $Pro^{B28}$ is provided in SEQ ID NO: 29.

SEQ ID NO: 29
$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Arginine, Norleucine, aminobutyric acid, aminopropionic acid, Alanine, or Glutamic Acid; where $Xaa_4$ is Alanine, Arginine, Aspartic Acid or Glutamic Acid; and where $Xaa_5$ is a derivative of the D or L stereoisomer of Lysine, Ornithine, di-aminobutyric acid or di-aminopropionic acid whose side chain amino group is linked to a diol-containing reagent.

The amino-acid sequence of a variant B chain modified by diol-containing reagent at residue B32 with alternative placement of Proline at position B29 is provided in SEQ ID NO: 30.

SEQ ID NO: 30
$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-Pro-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Alanine, Arginine, Aspartic Acid, or Glutamic Acid; where $Xaa_4$ is Alanine, Arginine, Aspartic Acid or Glutamic Acid; and where $Xaa_5$ is a derivative of the D or L stereoisomer of Lysine, Ornithine, di-aminobutyric acid or di-aminopropionic acid whose side chain amino group is linked to a diol-containing reagent.

The amino-acid sequence of a variant B chain modified by a diol-containing reagent at a sulfur-containing residue at position B32 while retaining $Pro^{B28}$ is provided in SEQ ID NO: 31.

SEQ ID NO: 31
$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-Pro-$Xaa_3$-Thr-$Xaa_4$-$Xaa_5$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid, Norleucine, aminobutyric acid, aminopropionic acid, Alanine, or Glutamic Acid; where $Xaa_4$ is Alanine, Arginine, Aspartic Acid or Glutamic Acid; and where $Xaa_5$ is a derivative of the D or L stereoisomer of Cysteine or Homocysteine whose side-chain sulfur atom is linked to a diol-containing reagent.

The amino-acid sequence of a variant B chain modified by diol-containing reagent at a sulfur-containing residue at position B32 with alternative placement of Proline at position B29 is provided in SEQ ID NO: 32.

SEQ ID NO: 32

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Pro-Thr-Xaa$_4$-Xaa$_5$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of Phe$^{B1}$; where Xaa$_2$ is Phenylalanine, penta-fluoro-Phe, 2-chloro-Phe, 2-bromo-Phe, 4-chloro-Phe, 2-methyl-Phe, or Cyclohexanylalanine; where Xaa$_3$ is Alanine, Arginine, Aspartic Acid, or Glutamic Acid; where Xaa$_4$ is Alanine, Arginine, Aspartic Acid or Glutamic Acid; and where Xaa$_5$ is a derivative of the D or L stereoisomer of Cysteine or Homocysteine whose side-chain sulfur atom is linked to a diol-containing reagent.

The amino-acid sequence of a variant B chain modified by diol-containing reagent at a basic residue at position B29 is given in SEQ ID NO: 33.

SEQ ID NO: 33

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Xaa$_4$-Thr-Xaa$_5$-Xaa$_6$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of Phe$^{B1}$; where Xaa$_2$ is Phenylalanine, penta-fluoro-Phe, 2-chloro-Phe, 2-bromo-Phe, 4-chloro-Phe, 2-methyl-Phe, or Cyclohexanylalanine; where Xaa$_3$ is Proline, Alanine, Arginine, Aspartic Acid, or Glutamic Acid; where Xaa$_4$ is a derivative of the D or L stereoisomer of Lysine, Ornithine, di-aminobutyric acid or di-aminopropionic acid whose side chain amino group is linked to a diol-containing reagent; and where Xaa$_5$-Xaa$_6$ represent optional one- or two-residue extensions of the B chain where Xaa$_5$ (if elected to be present) may be Glu, Gln, Gly, Ala, or Ser and where Xaa$_5$-Xaa$_6$ (if elected to be present) is drawn from the same set of amino acids such that at least one extended position is Glutamic Acid.

The amino-acid sequence of a variant des-B30 B chain modified by diol-containing reagent at a basic residue at position B29 is given in SEQ ID NO: 34.

SEQ ID NO: 34

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Xaa$_4$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of Phe$^{B1}$; where Xaa$_2$ is Phenylalanine, penta-fluoro-Phe, 2-chloro-Phe, 2-promo-Phe, 4-chloro-Phe, 2-methyl-Phe, or Cyclohexanylalanine; where Xaa$_3$ is Proline, Alanine, Arginine, Aspartic Acid, or Glutamic Acid; and where Xaa$_4$ is a derivative of the D or L stereoisomer of Lysine, Ornithine, di-aminobutyric acid or di-aminopropionic acid whose side chain amino group is linked to a diol-containing reagent.

The amino-acid sequence of a variant B chain modified by a diol-containing reagent at a sulfur-containing residue at position B29 is provided in SEQ ID NO: 35.

SEQ ID NO: 35

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Xaa$_4$-Thr-Xaa$_5$-Xaa$_6$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of Phe$^{B1}$; where Xaa$_2$ is Phenylalanine, Penta-fluoro-Phe, 2-chloro-Phe, 2-bromo-Phe, 4-chloro-Phe, 2-methyl-Phe, or Cyclohexanylalanine; where Xaa$_3$ is Proline, Lysine, Ornithine, Arginine, di-amino-butyric acid, di-amino-propionic acid, Norleucine, aminobutyric acid, aminopropionic acid, Alanine, Aspartic Acid or Glutamic Acid; where Xaa$_4$ is a derivative of the D or L stereoisomer of Cysteine or Homocysteine whose side-chain sulfur atom is linked to a diol-containing reagent; and where Xaa$_5$-Xaa$_6$ represent optional one- or two-residue extensions of the B chain where Xaa$_5$ (if elected to be present) may be Glu, Gln, Gly, Ala, or Ser and where Xaa$_5$-Xaa$_6$ (if elected to be present) is drawn from the same set of amino acids such that at least one extended position is Glutamic Acid.

The amino-acid sequence of a variant des-B30 B chain modified by a diol-containing reagent at a sulfur-containing residue at position B29 is provided in SEQ ID NO: 36.

SEQ ID NO: 36

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Xaa$_4$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of Phe$^{B1}$; where Xaa$_2$ is Phenylalanine, penta-fluoro-Phe, 2-chloro-Phe, 2-bromo-Phe, 4-chloro-Phe, 2-methyl-Phe, or Cyclohexanylalanine; where Xaa$_3$ is Proline, Lysine, Ornithine, Arginine, di-amino-butyric acid, di-amino-propionic acid, Norleucine, aminobutyric acid, aminopropionic acid, Alanine, Aspartic Acid or Glutamic Acid; and where Xaa$_4$ is a derivative of the D or L stereoisomer of Cysteine or Homocysteine whose side-chain sulfur atom is linked to a diol-containing reagent.

The amino-acid sequence of a variant B chain modified by diol-containing reagent at a sulfur-containing residue at position B28 is provided in SEQ ID NO: 37.

SEQ ID NO: 37

Xaa$_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly-

Xaa$_2$-Phe-Tyr-Thr-Xaa$_3$-Xaa$_4$-Thr-Xaa$_5$-Xaa$_6$

Where Xaa$_1$ is either the native α-amino group of Phe$^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Cysteine or Homocysteine whose side-chain sulfur atom is linked to a diol-containing reagent; where $Xaa_4$ is Lysine, Proline, Arginine, Alanine, Arginine, Aspartic Acid, Glutamic Acid, Norleucine, aminobutyric acid, aminopropionic acid, Ornithine, di-aminobutyric acid, or di-aminopropionic acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant des-B30 B chain modified by diol-containing reagent at a sulfur-containing residue at position B28 is provided in SEQ ID NO: 38.

SEQ ID NO: 38

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Cysteine or Homocysteine whose side-chain sulfur atom is linked to a diol-containing reagent; and where $Xaa_4$ is Lysine, Proline, Arginine, Alanine, Arginine, Aspartic Acid, Glutamic Acid, Norleucine, aminobutyric acid, aminopropionic acid, Ornithine, di-aminobutyric acid, or di-aminopropionic acid.

The amino-acid sequence of a variant des-[B29, B30] B chain modified by diol-containing reagent at a sulfur-containing residue at position B28 is provided in SEQ ID NO: 39.

SEQ ID NO: 39

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; and Where $Xaa_3$ is a derivative of the D or L stereoisomer of Cysteine or Homocysteine whose side-chain sulfur atom is linked to a diol-containing reagent.

The amino-acid sequence of a variant B chain modified by diol-containing reagent diol-containing reagent at a basic residue at position B28 is provided in SEQ ID NO: 40.

SEQ ID NO: 40

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is a derivative of the D or L stereoisomer of Lysine, Ornithine, di-aminobutyric acid or di-aminopropionic acid whose side chain amino group is linked to a diol-containing reagent; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant des-B30 B chain modified by diol-containing reagent diol-containing reagent at a basic residue at position B28 is provided in SEQ ID NO: 41.

SEQ ID NO: 41

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-promo-Phe, 4-chloro-Phe, 2-methyl-Phe, or Cyclohexanylalanine; where $Xaa_3$ is a derivative of the D or L stereoisomer of Lysine, Ornithine, di-aminobutyric acid or di-aminopropionic acid whose side chain amino group is linked to a diol-containing reagent; and where $Xaa_4$ is Lysine, Proline, Arginine, Alanine, Arginine, Aspartic Acid, Glutamic Acid, Norleucine, aminobutyric acid, aminopropionic acid, Ornithine, di-aminobutyric acid, or di-aminopropionic acid.

The amino-acid sequence of a variant des-[B29, B30] B chain modified by diol-containing reagent diol-containing reagent at a basic residue at position B28 is provided in SEQ ID NO: 42.

SEQ ID NO: 42

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$

Where $Xaa_1$ is either the native α-amino group of Phe or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; and where $Xaa_3$ is a derivative of the D or L stereoisomer of Lysine, Ornithine, di-aminobutyric acid or di-aminopropionic acid whose side chain amino group is linked to a diol-containing reagent.

The amino-acid sequence of a variant B chain modified by diol-containing reagent at a basic residue at position B29 is given in SEQ ID NO: 43.

SEQ ID NO: 43

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Proline, Alanine, Arginine, Aspartic Acid, or Glutamic Acid; where $Xaa_4$ is a derivative of the D or L stereoisomer of Lysine, Ornithine, di-aminobutyric acid or di-aminopropionic acid whose side chain amino group is linked to a diol-containing reagent; and where $Xaa_5$-$Xaa_6$-represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant des-B30 B chain modified by diol-containing reagent at a basic residue at position B29 is given in SEQ ID NO: 44.

SEQ ID NO: 44

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Proline, Alanine, Arginine, Aspartic Acid, or Glutamic Acid; and where $Xaa_4$ is a derivative of the D or L stereoisomer of Lysine, Ornithine, di-aminobutyric acid or di-aminopropionic acid whose side chain amino group is linked to a diol-containing reagent.

The amino-acid sequence of a variant B chain modified by a diol-containing reagent at a sulfur-containing residue at position B29 while retaining $Pro^{B28}$ is provided in SEQ ID NO: 45.

SEQ ID NO: 45

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine, Ornithine, Arginine, di-amino-butyric acid, di-amino-propionic acid. Norleucine, aminobutyric acid, aminopropionic acid, Alanine, or Glutamic Acid; where $Xaa_3$ is Alanine, Arginine, Aspartic Acid or Glutamic Acid; where $Xaa_4$ is a derivative of the D or L stereoisomer of Cysteine or Homocysteine whose side-chain sulfur atom is linked to a diol-containing reagent; and where $Xaa_5$-$Xaa_6$ represent optional one- or two-residue extensions of the B chain where $Xaa_5$ (if elected to be present) may be Glu, Gln, Ala, or Ser and where $Xaa_5$-$Xaa_6$ (if elected to be present) is drawn from the same set of amino acids such that at least one extended position is Glutamic Acid.

The amino-acid sequence of a variant des-B30 B chain modified by a diol-containing reagent at a sulfur-containing residue at position B29 is provided in SEQ ID NO: 46.

SEQ ID NO: 46

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Lysine. Ornithine, Arginine, di-amino-butyric acid, di-amino-propionic acid, Norleucine, aminobutyric acid, aminopropionic acid, Alanine, or Glutamic Acid; where $Xaa_3$ is Alanine, Arginine, Aspartic Acid or Glutamic Acid; and where $Xaa_4$ is a derivative of the D or stereoisomer of Cysteine or Homocysteine whose side-chain sulfur atom is linked to a diol-containing reagent.

The amino-acid sequence of a variant B chain modified by O-linked glycosylation at residue B28 is provided in SEQ ID NO: 47.

SEQ ID NO: 47

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $O^{\beta}$-$Thr^{B28}$-linked or $O^{\beta}$-$Ser^{B28}$-linked monosaccharide pyranoside selected from a group consisting of α-D-mannopyranoside, α-D-glucopyranoside, or N-acetyl-β-D-galactopyranoside, or where $Xaa_3$ is an $O^{\beta}$-$Thr^{B28}$-linked or $O^{\beta}$-$Ser^{B28}$-linked disaccharide containing one or more of the above monosaccharide subunits; where $Xaa_4$ is Arginine, Ornithine, di-aminobutyric acid, di-aminopropionic acid, Proline, Alanine, Aspartic Acid, Glutamine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B28 is provided in SEQ ID NO: 48.

SEQ ID NO: 48

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is an $N^{\beta}$-$Asn^{B28}$-linked or $N^{\gamma}$-$Gln^{B28}$-linked monosaccaride pyranoside selected from a group consisting of α-D-mannopyranoside, α-D-glucopyranoside, or N-acetyl-β-D-galactopyranoside, or where $Xaa_3$ is an $N^{\beta}$-$Asn^{B28}$-linked or $N^{\gamma}$-$Gln^{B28}$-linked disaccharide containing one or more of the above monosaccharide subunits; where $Xaa_4$ is Arginine, Ornithine, di-aminobutyric acid, di-aminopropionic acid, Proline, Alanine, Aspartic Acid, Glutamine, or Glutamic Acid; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by O-linked glycosylation at residue B29 is provided in SEQ ID NO: 49.

SEQ ID NO: 49

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Arginine, Ornithine, di-aminobutyric acid, di-aminopropionic acid, Proline, Alanine, Aspartic Acid, Glutamine, or Glutamic Acid; where $Xaa_4$ is an $O^{\beta}$-$Thr^{B29}$-linked or $O^{\beta}$-$Ser^{B29}$-linked monosaccaride pyranoside selected from a group consisting of α-D-mannopyranoside, α-D-glucopyranoside, or N-acetyl-β-D-galactopyranoside, or where $Xaa_3$ is an $O^{\beta}$-$Thr^{B29}$-linked or $O^{\beta}$-$Ser^{B29}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of a variant B chain modified by N-linked glycosylation at residue B29 is provided in SEQ ID NO: 50.

SEQ ID NO: 50

$Xaa_1$-Phe-Val- Glu-Gln-His-Leu-Cys-Gly-Ser-His-Leu-

Val-Glu-Ala-Leu-Tyr-Leu-Val-Cys-Gly-Glu-Arg-Gly- $Xaa_2$-Phe-Tyr-Thr-$Xaa_3$-$Xaa_4$-Thr-$Xaa_5$-$Xaa_6$

Where $Xaa_1$ is either the native α-amino group of $Phe^{B1}$ or optionally a phenylboronic-acid moiety or halogenic derivative of a phenylboronic-acid moiety connected by peptide linkage or optional acyl linker to the α-amino group of $Phe^{B1}$; where $Xaa_2$ is Phenylalanine, penta-fluoro-Phe, 2-chloro-Phe, 2-bromo-Phe, 4-chloro-Phe, 2-methyl-Phe, or Cyclohexanylalanine; where $Xaa_3$ is Arginine, Ornithine, di-aminobutyric acid, di-aminopropionic acid, Proline, Alanine, Aspartic Acid, Glutamine, or Glutamic Acid; where $Xaa_4$ is an $N^{\beta}$-$Asn^{B29}$-linked or $N^{\gamma}$-$Gln^{B29}$-linked monosaccaride pyranoside selected from a group consisting of α-D-mannopyranoside, α-D-glucopyranoside, or N-acetyl-β-D-galactopyranoside, or where $Xaa_3$ is an $N^{\beta}$-$Asn^{B29}$-linked or $N^{\gamma}$-$Gln^{B29}$-linked disaccharide containing one or more of the above monosaccharide subunits; and where $Xaa_5$-$Xaa_6$ represent optional one- or two-residue extensions of the B chain where $Xaa_5$ (if elected to be present) may be Glu, Gln, Gly, Ala, or Ser and where $Xaa_5$-$Xaa_6$ (if elected to be present) is drawn from the same set of amino acids such that at least one extended position is Glutamic Acid.

The amino-acid sequence of variant A chain of human insulin modified by a phenylboronic acid at the α-amino group of $Gly^{A1}$ is provided as SEQ ID NO: 51.

SEQ ID NO: 51

$Xaa_1$-Gly-Ile-Val-Glu-Gln-Cys-Cys-$Xaa_2$-Ser-Ile-Cys-

Ser-$Xaa_3$-$Xaa_4$-Gln-Leu-$Xaa_5$-Asn-Tyr-Cys-$Xaa_6$

Where $Xaa_1$ is a phenylboronic-acid moiety or halogenic derivative of a phenylboronic-acid moiety connected by peptide linkage or optional acyl linker to the α-amino group of $Gly^{A1}$; where $Xaa_2$ is Threonine, Alanine, Histidine, Glutamine, Arginine, or Glutamic Acid; where $Xaa_3$ is Leu or Trp; where $Xaa_4$ is Tyrosine, Alanine or Glutamic Acid; where $Xaa_5$ is Glutamic Acid, Glutamine or Arginine; and where $Xaa_6$ is Asparagine, Aspartic Acid, Alanine or Glycine.

The amino-acid sequence of variant A chain of human insulin modified by a phenylboronic acid at the side-chain amino group of a basic residue at position A4 is provided as SEQ ID NO: 52.

SEQ ID NO: 52

Gly-Ile-Val-$Xaa_1$-Gln-Cys-Cys-$Xaa_2$-Ser-Ile-Cys-

Ser-$Xaa_3$-$Xaa_4$-Gln-Leu-$Xaa_4$-Asn-Tyr-Cys-$Xaa_5$

Where $Xaa_1$ is a phenylboronic-acid moiety or halogenic derivative of a phenylboronic-acid moiety connected by to the side-chain amino group of Lysine, Ornithine, di-aminobutyric acid or di-aminopropionic acid; where $Xaa_2$ is Threonine, Alanine, Histidine, Glutamine, Arginine, or Glutamic Acid; where $Xaa_3$ is Leu or Trp; where $Xaa_4$ is Tyrosine, Alanine or Glutamic Acid; where $Xaa_5$ is Glutamic Acid, Glutamine or Arginine; and where $Xaa_6$ is Asparagine, Aspartic Acid, Alanine or Glycine.

The amino-acid sequence of variant A chain of human insulin is provided as SEQ ID NO: 53.

SEQ ID NO: 53

```
Xaa1-Ile-Val-Glu-Gln-Cys-Cys-Xaa2-Ser-Ile-Cys-

Ser-Xaa3-Xaa4-Gln-Leu-Xaa4-Asn-Tyr-Cys-Xaa5
```

Where $Xaa_1$ is a basic residue selected from the group consisting of D-Lysine, L-Lysine, D-Ornithine, L-Ornithine, D-di-amino-propionic acid, L-di-aminopropionic acid whose side chain amino group is derivatized by a phenylboronic acid moiety optionally including a halogenic modification and optionally attached via an acyl linker; where $Xaa_2$ is Threonine, Alanine, Histidine, Glutamine, Arginine, or Glutamic Acid; where $Xaa_3$ is Leu or Trp; where $Xaa_4$ is Tyrosine, Alanine or Glutamic Acid; where $Xaa_5$ is Glutamic Acid, Glutamine or Arginine; and where $Xaa_6$ is Asparagine, Aspartic Acid, Alanine or Glycine.

Analogues of insulin containing α-D-mannopyranoside, α-D-glucopyranoside, and/or N-acetyl-β-D-galactopyranoside as $O^{\beta}$-linked adducts of Threonine were prepared by trypsin-mediated semi-synthesis. The protocol for semi-synthesis employed a des-octapeptide[B23-B30] fragment of human insulin or insulin analogue together with a synthetic peptide containing an N-terminal Glycine (octapeptide, nonapeptide, or decapeptide) and a monosaccaride adduct at $Thr^{B27}$ and/or $Thr^{B30}$. The des-octapeptide[B23-B30] fragment contains the three native disulfide bridges of wild-type insulin; the protocol including purification of the fragment, peptide, and product by high-performance liquid chromatography was a modification of that described (Mirmira, R. G., and Tager, H. S., 1989. *J. Biol. Chem.* 264: 6349-6354.) This protocol employs (i) a synthetic peptide containing a. monosaccaride pyranoside adduct (SEQ ID NO: 53-65) and (ii) truncated analogue des-tripeptide[B1-B3]-des-octapeptide[B23-B30]-insulin, or in the case of [HisA4, $His^{A8}$, $Gly^{A21}$]-insulin analogues, [HisA4, $His^{A8}$, $Gly^{A21}$]-des-tripeptide[B1-B3]-des-octapeptide[B23-B30]-insulin, or in the case of $Gln^{B13}$-insulin analogues, $Gln^{B13}$-des-tripeptide[B1-B3]-des-octapeptide[B23-B30]-insulin, or in the case of $His^{A8}$-insulin analogues. The following literature is cited to demonstrate that the testing and assay methods described herein would be understood by one of ordinary skill in the art.

NHS activation of Phenylboronic Acid

To prepare insulin analogues in which the α-amino group of $Gly^{A1}$ was modified by a FPA, a protocol was developed with three steps.

(i) Step 1: Activation of the PBA Reagent.

Activation of 4-carboxy-3-fluoro-phenylboronic acid pinacol ester (PBA; purchased from Combi-Blocks, San Diego, Calif.) to a species amenable to coupling was achieved with N-hydroxysuccinamide (NHS) (Sigma Aldrich, St. Louis, Mo.). We illustrate this step as follows. To this end, PBA (300 mg, 1.126 mmol) was dissolved in 4.4 mL ethyl acetate and incubated at 4° C. for 20 minutes. To this reaction mixture, 131 mg (1.14 mmol) NHS and 247 mg (1.86 mmol) dicyclohexyl carbodiimide (DCC) (Sigma Aldrich, St. Louis, Mo.) were added. The solution was stirred at room temperature overnight. N,N'-dicyclohexyl urea byproduct was removed via centrifugation for 5 minutes at 13,500 rpm in an Eppendorf® microfuge. The solvent was removed ex vacuo. PBA-N-hydroxysuccinimide ester was purified by recrystallization from acetone and n-hexane. Product was made 30 mg/ml in acetonitrile.

Step 2: Coupling (7: Activated PRA to N-terminus or N-termini of an Insulin Fragment.

Des[B23-B30]-octapeptide insulin (DOI) (5 mg in 100 μl of 0.1 M sodium carbonate at pH 7.6) was combined with 100 μl of NHS-ester of PBA (30 mg/ml) in acetonitrile. The solution was agitated at 25° C. for 2 hours, The reaction was halted at a stage in which there were both single- and double-derivatized DOI molecules; these were resolved and individually purified by reverse-phase high-performance liquid chromatography (HPLC). A Waters® 2535 quaternary-gradient chromatography system was used with a Higgins Analytical® Proto 300 C4 column (10 μm, 250×20 mm). A two-buffer mobile phase was used for purification: aqueous 0.1% trifluoroacetic acid (TFA; buffer A) and 0.1% TFA in acetonitrile (buffer B) with a gradient of 5-95% buffer B over 40 minutes. Protein elution time was monitored by LIV absorbance at 215 and 280 nm using a Waters 2489 UV/Vis detector. Single- and double-coupled molecules were eluted at 18 minutes and 19.5 minutes, respectively. Identities of protein products were confirmed by MALDI-TOF mass spectrometry using an Applied Biosystems® 4700 Proteomics Analyzer. A saturated solution of α-cyano-4-hydroxycinnamic acid (α-CHCA) (Sigma-Aldrich, St. Louis, Mo.) in 50% acetonitrile 0.1% TFA was used as matrix. Masses showed loss of two hydroxyl groups associated with anhydride formation upon laser desorption as previously reported (Hoeg-Jensen, et al). (Mass of Single-Coupled DOI: 4997, Mass of Double-Coupled DOI: 5127) The reaction was found to couple PBA to the N-terminus of the A-chain before coupling to the B-chain. Identity of the single-coupled analog was confirmed after reduction with 50 mM dithiothreitol (DTT) in 1×PBS pH 7.4 for 1 hour at room temperature. Protein was desalted using Millipore® C18 ZipTip® pipette tips and eluted into 5 μL α-CHCA matrix. Masses of individual polypeptide chains were confirmed with MALDI-TOF mass spectrometry (mass PBA-coupled A-chain: 2515, mass B-chain: 2488). Samples were lyophilized using a Labconco® Freezezone 6® lyophilizer.

Step 3: Trypsin-mediated Semi-synthesis.

The desired insulin analogs were prepared by trypsin-mediated semi-synthesis as described above.

To evaluate the kinetic properties pertaining to the disassembly of insulin analogue hexamer, visual absorption spectroscopy was employed as described by Richards, J. P., et al. ("Self-association properties of monomeric insulin analogs under formulation conditions." *Pharm. Res.* 15:1434-41; 1998.) In brief, visual absorption spectroscopy provides a convenient probe to monitor the formation and disassembly of phenol-stabilized $R_6$ $Co^{2+}$-substituted insulin hexamers. To this end, insulin analogues were made 0.6 mM in a buffer containing 50 mM Tris-HCl (pH 7.4), 50 mM phenol, 0.2 mM $CoCl_2$, and 2 mM NaSCN in the absence of glucose or in the presence of 25 mM glucose. The sample pH was in each case 7.4, and samples were incubated overnight at room temperature prior to the studies to ensure that a conformational equilibrium was reached. Spectra (400-750 nm) were obtained to monitor tetrahedral $Co^{2+}$ coordination with its signature d-d absorption band at or near 574 nm. To determine the rate of $Co^{2+}$ release from the hexamers, metal-ion sequestration was initiated at 33° C. (to simulate subcutaneous temperatures) by addition of an aliquot of an EDTA stock solution (50 mM at pH 7.4) to a final EDTA concentration 2 mM (i.e., in excess of the total concentration of cobalt ions). Attenuation of the 574-nm absorption band was monitored on a time scale of seconds to hours. Postdissociation absorption spectra (400-750 nm) were collected to confirm complete attenuation of the d-d absorption band. Kinetic data were fit to mono-exponential decay functions to determine dissociation rates (or equivalently the half-life of $Co^{2+}$ coordinated variant insulin $R_6$ hexamers).

Rodent Assays—Male Lewis rats (mean body mass~300 g) were rendered diabetic by treatment with streptozotocin (STZ) as described (35). To test the in vivo potency of insulin analogs in relation to Orn$^{B29}$-insulin or Nle$^{B29}$-insulin, protein solutions containing insulin analogs were constituted in a buffer composed of 16 mg glycerin, 1.6 mg meta-cresol. 0.65 mg phenol and 3.8 mg sodium phosphate (pH 7.4), Insulin analogs were injected intravenously (IV) into tail veins at a dose of 10 μg per 100 μl of buffer per 300 g rat. The resulting changes in blood-glucose concentration were monitored by serial measurements using a clinical glucometer (EasyMax Voice Blood Glucose Meter) over the next several hours. Insulin analogs were each re-purified by reverse-phase HPLC, dried to powder, dissolved in diluent at the same maximum protein concentration and re-quantitated by analytical C4 reverse-phase HPLC; dilutions were made using the above buffer.

Rats were injected IV at time t=0. Blood was obtained from the clipped tip of the tail at time t=0 and every 10 min for the first hour, every 20 min for the second hour, every 30 min for the third hour and every hour thereafter up to 360 min. Although studies of the high-affinity natural analogs were limited in size (N=5 rats), the impact of the iodo-Tyr$^{B26}$ modification was evaluated with greater power. Studies of the 3-I-Tyr$^{B26}$-Nle$^{B29}$-insulin were thus repeated (in relation to Nle$^{B29}$-insulin) on four dates over six months to avoid confounding variables that may impact the environment of the rat colony week to week. Rats studied on each date (N=4 or 5) were obtained at random from a large colony (50 rats). Levels of mean glycemia at baseline were similar in each group and at each date; similar individual trends were observed at each date. The efficacy of insulin action in reducing blood-glucose concentration was calculated using (a) the change in concentration over the first hour (d[glucose]/dt); (b) the integrated area between the glucose time dependence and a near-horizontal line from the starting blood glucose concentration to the final concentration; and (c) the integrated area for the same curve in the first 0-80 min versus that observed in the 80-360 min interval (the latter representing the delayed "tail" of insulin action). Areas under the linear upper hyperglycemic baseline and above the curve representing observed blood-glucose concentrations were estimated by trapezoidal approximation and denoted AOC. Assessment of statistical significance was performed using Student's t-test.

Our in vitro insulin receptor-binding assay employed solubilized insulin receptor (isoform B) with C-terminal streptavidin-binding protein tags purified by sequential wheat-germ agglutinin (WGA) and Streptactin-affinity chromatography from detergent lysates of polyclonal stably transfected 293PEAK cell lines expressing the insulin receptor isoform. A dilution series of insulin analogue (11 dilutions, 5-fold each with a maximum final concentration of 2 μM) in 100 μl binding buffer (100 mM HEPES (pH 7.8), 100 mM NaCl, 10 mM $MgSO_4$, 0.025% (v/v) Tween 20 and 0.5% (w/v) bovine serum albumin) was made in a 96-well plate (Costar). The assay was initiated by addition to the wells of 100 μl binding buffer and supplemented by (i) WGA scintillation-proximity-assay (SPA) beads (Perkin Elmer), (ii) solubilized receptor, and (iii) $^{125}$I-Tyr$^{A14}$-insulin as a radiolabeled tracer. The final concentration of [$^{125}$I]-labeled ligand was 7.5 pM, and the amount of receptor added was adjusted so that the extent of labeled ligand binding in the absence of competitor was <15% of the total added counts in order to avoid ligand-depletion artifacts. Plates were incubated with gentle shaking for 24 h at room temperature, centrifuged, and counted for 5 mm/well in a 12-detector Trilux scintillation counter (Perkin Elmer/Wallac). To obtain analogue dissociation constants, competitive binding data were analyzed by non-linear regression.

What is claimed is:

1. An insulin analogue containing a modified A-chain polypeptide and a modified B-chain polypeptide, wherein the A-chain is modified with a monomeric glucose-binding moiety at or within 5 residues of the A-chain N-terminus, and wherein the B-chain is modified with a diol-containing modification or an alpha-hydroxycarboxylate modification at or within 6 residues of the B-chain C-terminus.

2. The insulin analogue of claim 1, wherein the diol-containing modification is conjugated through the side chain of a D-amino acid containing a thiol group or containing an amino group.

3. The insulin analogue of claim 2, wherein the D-amino acid is D-Cysteine, D-Homocysteine, D-Lysine, D-Ornithine, D-diaminobutyric acid, or D-diaminopropionic acid.

4. The insulin analogue of claim 1, wherein the monomeric glucose-binding moiety comprises phenylboronic acid or a halogen-modified phenylboronic acid derivative.

5. The insulin analogue of claim 4, wherein the monomeric glucose-binding moiety is conjugated to the insulin A chain through a spacer element, which is optionally an acyl group having from 1 to 16 carbon atoms.

6. The insulin analogue of claim 1, wherein the monomeric glucose-binding moiety is linked to an alpha-amino functional group.

7. The insulin analogue of claim 6, wherein the monomeric glucose-binding moiety is linked to the side-chain amino function of a D-Lysine, D-Ornithine, D-diaminobutyric acid, or D-diaminopropionic acid substituted at position Al, to the side-chain amino function of a L-Lysine, L-Ornithine, L-diaminobutyric acid, or L-diaminopropionic acid substituted at position A4.

8. The insulin analogue of claim 1, wherein:

the monomeric glucose-binding moiety is linked simultaneously to the alpha-amino function of residue B1, or the insulin has a deletion of residue B1 and the monomeric glucose-binding moiety is linked simultaneously to the alpha-amino function of residue B2, or the insulin has a deletion of residues B1 and B2 and the monomeric glucose-binding moiety is linked simultaneously to the alpha-amino function of residue B3, or the insulin has a deletion of residues B1-B3 and the monomeric glucose-binding moiety is linked simultaneously to the alpha-amino function of residue B4.

9. The insulin analogue of claim 1, whose B chain conforms to any one of SEQ ID NOS: 7-50 and whose A chain conforms to any one of SEQ ID NOS 51-53.

10. The insulin analogue of claim 1, wherein the diol-containing modification is a monosaccharide, disaccharide or oligosaccharide.

11. The insulin analogue of claim 1, wherein the diol-containing modification is attached to the side chain of Ser, Thr, Asn, Gln, Cys or Homocysteine.

12. The insulin analogue of claim 11, wherein the diol-containing modification is attached through the side chain or ThrB27, ThrB30, or an amino acid within a two-residue extension of the B chain.

13. The insulin analogue of claim 10, wherein the diol-containing modification is a monosaccharide selected from glucose, mannose, and N-acetyl-galactose.

14. The insulin analogue of claim 10, wherein the diol-containing modification is a disaccharide selected from glucose-glucose, mannose-mannose, glucose-mannose, and mannose-glucose.

15. The insulin analogue of claim 10, wherein the diol-containing modification is a branched oligosaccharide.

16. A pharmaceutical composition, comprising an effective amount of the insulin analogue of claim 1, and a pharmaceutically acceptable carrier or excipient, optionally formulated for sub-cutaneous injection.

17. A method of treating a patient comprising administering the pharmaceutical composition of claim 16 to a patient in need of treatment.

18. A formulation of claim 16 wherein the formulation contains zinc ions at a molar ratio of between 0.00 and 0.50 zinc ions per insulin analogue monomer and wherein the pH of the formulation is between pH 3.0 and pH 4.2.

19. A method of preparation of an insulin analogue containing a modified A-chain polypeptide and a modified B-chain polypeptide, wherein the A-chain is modified with a monomeric glucose-binding moiety at or within 5 residues of the A-chain N-terminus, and wherein the B-chain is modified with a diol-containing modification or an alpha-hydroxycarboxylate modification at or within 6 residues of the B-chain C-terminus, the method comprising (a) providing a des-octapeptide[B23-B30] fragment of insulin or insulin analogue;

(b) providing a saccharide ester of phenylboronic acid;

(c) incubating the des-octapeptide[B23-B30] fragment of insulin or insulin analogue and saccharide ester of phenylboronic acid under conditions conducive to coupling of phenylboronic acid to the des-octapeptide [B23-B30] fragment of insulin or insulin analogue to provide a phenylboronic acid coupled to the N-terminus of the insulin A-chain of the des-octapeptide[B23-B30] fragment of insulin or insulin analogue;

(d) providing a synthetic peptide of length 6-10 amino-acid residues whose N-terminal residue is Glycine and which upon modification contains no tryptic cleavage site, and wherein the peptide incorporates an N-linked or O-linked saccharide; and (e) incubating the synthetic peptide with the des-octapeptide[B23-B30] fragment of insulin or insulin analogue in the presence of trypsin under conditions conducive to the enzymatic activity of trypsin such that trypsin catalyzes the formation of a bond between synthetic peptide and the des-octapeptide[B23-B30] fragment of insulin or insulin analogue.

20. The method of claim 19, wherein the des-octapeptide [B23-B30] fragment of insulin or insulin analogue is obtained by trypsin digestion of a parent insulin or insulin analogue.

* * * * *